United States Patent [19]
Everhart et al.

[11] Patent Number: 5,855,788
[45] Date of Patent: Jan. 5, 1999

[54] CHEMICALLY CHARGED-MODIFIED FILTER FOR REMOVING PARTICLES FROM A LIQUID AND METHOD THEREOF

[75] Inventors: Dennis Stein Everhart, Alpharetta; Elizabeth Deibler Gadsby, Marietta; Rosann Marie Kaylor, Cumming; Kristi Lynn Kiick-Fischer, Alpharetta, all of Ga.

[73] Assignee: Kimberly-Clark Worldwide, Inc., Neenah, Wis.

[21] Appl. No.: 594,879

[22] Filed: Feb. 7, 1996

[51] Int. Cl.$^6$ ............ B01D 61/00; B01D 39/02
[52] U.S. Cl. ............ 210/653; 210/651; 210/679; 210/691; 210/503; 210/504; 210/505; 210/508; 210/500.37; 210/500.36; 210/490; 210/502.1
[58] Field of Search ............ 210/502.1, 767, 210/777, 650–653, 501, 490, 503–508, 500.36, 500.37, 685, 679, 691, 764; 428/152, 198, 219, 326, 903; 442/329, 382

[56] References Cited

U.S. PATENT DOCUMENTS

| | | | |
|---|---|---|---|
| 2,262,770 | 11/1941 | La Piana | 260/6 |
| 2,262,771 | 11/1941 | La Piana | 260/6 |
| 2,310,795 | 2/1943 | La Piana et al. | 106/146 |
| 2,453,752 | 11/1948 | La Piana et al. | 260/6 |
| 2,979,422 | 4/1961 | Bersin et al. | 117/106 |
| 3,104,154 | 9/1963 | Morimoto et al. | 18/54 |
| 3,188,233 | 6/1965 | Powers et al. | 117/140 |
| 3,202,748 | 8/1965 | Morio Naka et al. | 264/194 |

(List continued on next page.)

FOREIGN PATENT DOCUMENTS

| | | |
|---|---|---|
| 538901 | 4/1957 | Canada . |
| 0 099 699 | 2/1984 | European Pat. Off. . |
| 0199171 | 10/1986 | European Pat. Off. . |
| 0 280 560 | 8/1988 | European Pat. Off. . |
| 0 517 522 | 12/1992 | European Pat. Off. . |

(List continued on next page.)

OTHER PUBLICATIONS

Abstract JP 04 166 221 (NOK Corp.) Derwent Publications Ltd., London, GB, 12 Jun., 1992.
PCT Counterpart International Search Report mailed Jun. 16, 1997.
Abstract JP, A, 04 136 268, Derwent Publications Ltd., London, GB 11 May 1992.
*Textile Research Journal*, "Effect of Quaternized Amphiphilic Peptides on Pilling and Electrostatic Discharge of Wool Fabrics", vol. 64, No. 11, 1 Nov. 1994, pp. 648–652.
Theodore H. Meltzer, *Filtration in the Pharmaceutical Industry*, Marcel Dekker, Inc., New York, 1987, pp. 310–314.
Zaverio M. Ruggeri, Mechanisms of Shear–induced Platelet Adhesion and Aggregation, *Thrombosis and Haemostatis– Journal of the International Society of Thrombosis and Haemostasis*, Jul. 1, 1993, Schattauer Stuttgart, New York, 1993, pp. 119–123.

*Primary Examiner*—Robert J. Popovics
*Attorney, Agent, or Firm*—James E. Ruland

[57] ABSTRACT

A chemically charged-modified filter for removing charged, micron to sub-micron sized particles from an aqueous liquid, the filter being composed of a filter sheet having a plurality of individual exposed surfaces, at least a portion of which having a surface energy of less than about 45 dynes per centimeter; amphiphilic macromolecules adsorbed onto at least some individual exposed surfaces having a surface energy of less than about 45 dynes per centimeter; and chemical charge modifiers incorporated onto at least a portion of the amphiphilic macromolecules; so that when said charge-modified substrate is in contact with the aqueous liquid containing the charged, micron to sub-micron sized particles, said particles are adsorbed onto the chemically charge-modified filter. Also disclosed is a method of removing charged, micron to sub-micron sized particles from an aqueous liquid in which an aqueous liquid containing charged, micron to sub-micron sized particles is passed through a chemically charge-modified filter.

37 Claims, 6 Drawing Sheets

U.S. PATENT DOCUMENTS

| | | | |
|---|---|---|---|
| 3,494,775 | 2/1970 | Coscia et al. | 106/124 |
| 3,690,925 | 9/1972 | Morris | 117/76 T |
| 4,309,247 | 1/1982 | Hou et al. | 162/149 |
| 4,523,995 | 6/1985 | Pall et al. | 210/504 |
| 4,761,161 | 8/1988 | Potschke | 8/543 |
| 4,859,340 | 8/1989 | Hou et al. | 210/502.1 |
| 4,981,591 | 1/1991 | Ostreicher | 210/502.1 |
| 5,055,316 | 10/1991 | Hoffman et al. | 427/2 |
| 5,085,784 | 2/1992 | Ostreicher | 210/767 |
| 5,151,321 | 9/1992 | Reeves et al. | 428/286 |
| 5,208,075 | 5/1993 | Kroner et al. | 427/389.9 |
| 5,229,172 | 7/1993 | Cahalan et al. | 427/536 |
| 5,260,396 | 11/1993 | Kroner et al. | 527/201 |
| 5,342,646 | 8/1994 | Kleese et al. | 427/2.1 |

FOREIGN PATENT DOCUMENTS

| | | |
|---|---|---|
| 2 564 004 | 5/1984 | France . |
| 2364524 | 7/1974 | Germany . |
| 4108170 | 9/1992 | Germany . |
| 42-16065 | 9/1967 | Japan . |
| 45-34390 | 11/1970 | Japan . |
| 45-34391 | 11/1970 | Japan . |
| 4048590 | 12/1974 | Japan . |
| 7170904 | 10/1982 | Japan . |
| 425689 | 3/1935 | United Kingdom . |
| 96/12058 | 4/1996 | WIPO . |
| 96/28602 | 9/1996 | WIPO . |

CHEMICALLY CHARGED-MODIFIED FILTER FOR REMOVING PARTICLES FROM A LIQUID AND METHOD THEREOF

FIELD OF THE INVENTION

This invention relates to a filter for aqueous liquids and to a method of filtering aqueous liquids.

BACKGROUND OF THE INVENTION

Apertured films, woven fabrics and nonwoven materials have been used as filter sheets for removing or separating particles from liquids. Generally speaking, such filter sheets rely on some form of mechanical straining or physical entrapment. Such filter sheets can pose limitations when the size of the particle to be removed is small relative to the average pore diameter of the filter sheet (e.g., large pressure drops across the filter sheet). For nonwoven materials, this is particularly true for particles of less than one micron in diameter.

Improved filters have been developed with modified surface charge characteristics to capture and adsorb particles by electrokinetic interaction between the filter surface and particles contained in an aqueous liquid.

It would be desirable if certain inexpensive materials could be used to produce filters having modified surface charge characteristics for filtering very fine particles from aqueous liquids. For example, polyolefins are widely used in the manufacture of sheets of apertured films, woven fabrics, and nonwoven materials. Many types of polyolefin sheets tend to be hydrophobic and relatively inert. That is, the low surface free energy of polyolefins (e.g., polypropylene) and their relatively chemically inert nature render many unmodified polyolefins ill-suited for filter sheet applications in which a modified surface charge is desired for removing particles from an aqueous liquid.

For example, many chemical charge modifiers (e.g., cationic resins, charged particles, etc.) adhere poorly, if at all, to conventional unmodified, hydrophobic polyolefin sheets.

In the past, chemical coatings and/or internal additives have been added to filter sheets made of inexpensive materials to impart desired properties. Many of these coatings and/or additives present problems related to cost, effectiveness, durability and/or the environment.

It has been proposed that biofunctional materials (e.g., proteins) can be deposited from solutions onto different substrates (i.e., sheets of materials) to modify the surface properties of the substrates and/or serve as a functionalized surface that can be chemically reactive. However, many of the economically desirable substrates (e.g., substrates formed of polymers such as polyolefins) have surfaces that are unsuitable for the rapid and inexpensive deposition of biofunctional materials, especially when durable, tightly-bound coatings of satisfactory adherence are desired.

Even if inexpensive, durable, tenacious coatings could be adhered to an economically desirable substrate, coatings composed solely of biofunctional materials (e.g., proteins) may have limitations, especially if the coatings lacked the desired chemical characteristics such as, for example, modified surface charge characteristics.

Thus, there is still a need for a practical and inexpensive chemically charged modified filter for removing charged, micron to sub-micron sized particles from an aqueous liquid. A need exists for such a filter formed from an unmodified, relatively inert, hydrophobic substrate such as, for example, an unmodified, relatively inert, polyolefin substrate. A need also exists for a method of removing charged, micron to sub-micron sized particles from aqueous liquid utilizing a practical and inexpensive chemically charge modified filter such as, for example, a chemically charge-modified filter formed from an unmodified, relatively inert, polyolefin substrate.

In addition to the needs described above, there is a need for a simple, practical and inexpensive chemically charge-modified filter for removing waterborne pathogens from aqueous liquid. This need also extends to a simple method for removing waterborne pathogens from aqueous liquid utilizing a practical and inexpensive chemically charge-modified filter.

One phenomena observed with some filters having modified surface charge characteristics is that the filters have different filtration efficiencies for different types of waterborne pathogens, such as, for example, different types of bacteria. That is, some filters having modified surface charges provide acceptable removal of some types of waterborne pathogens (e.g., some types of bacteria) but not others. The nature of this affinity appears to be difficult to predict. Since even relatively small differences in waterborne pathogen removal efficiency can be important, the discovery that a filter or filter system has an unpredictably strong affinity for a waterborne pathogen would be both unexpected and highly desirable, especially if the filter can be used to produce potable water. Meeting this need is important because removing waterborne pathogens from aqueous liquids in a practical and inexpensive manner remains a challenge in many parts of the world.

Definitions

As used herein, the term "chemical charge modifier" refers to polyvalent cations, polyvalent anions, positively charged particles and/or negatively charged particles. Exemplary chemical charge modifiers may have a positive charge and, when present in a liquid having a dielectric constant sufficient for separate charged particles to exist, can be incorporated or adsorbed onto a negatively charged amphiphilic macromolecule (e.g., amphiphilic protein) coating on a substrate to modify the coating so that cationic species and/or positively charged particles are present at the surface of the coating under the appropriate conditions. Exemplary chemical charge modifiers include, but are not limited to, $Ca^{2+}$, $Al^{3+}$, $Bi^{3+}$ ions, and $AlO(OH)$, $Bi(OH)_3$, iron/magnesium(Fe/Mg) particles, cationic polymers such as, for example, quaternary amine containing cationic resins, and aliphatic amines having at least one primary amine and/or secondary amine, and the like. Generally speaking, when the chemical charge modifier/amphiphilic macromolecule (e.g., amphiphilic protein) coated substrate is in contact with aqueous liquid having a pH above the isoelectric point of the amphiphilic macromolecule (e.g., amphiphilic protein) component, cationic species and/or positively charged particles may be adsorbed via electrostatic or electrokinetic interactions between the negatively charged amphiphilic macromolecule coating and positively charged chemical charge modifier.

As used herein, the term "chemically charge-modified" refers to the incorporation of chemical charge modifiers (e.g., polyvalent cations, positively charged particles, cationic polymers and aliphatic amines having at least one primary amine and/or secondary amine, and the like) onto an amphiphilic macromolecule (e.g., amphiphilic protein) coating deposited on a relatively inert, hydrophobic substrate such as, for example, a polyolefin substrate. Generally speaking, charge modification occurs when the chemical charge modifier/amphiphilic macromolecule (e.g., amphiphilic protein) coated substrate is in contact with aqueous liquid having a pH above the isoelectric point of the amphiphilic macromolecule (e.g., amphiphilic protein) component.

As used herein, the term "waterborne pathogens" refers to microorganisms existing in water or aqueous liquids that are capable of causing disease. Exemplary waterborne pathogens include, but are not limited to, *Vibrio cholerae, Giardia lamblia*, and *Cryptosporidium parvum*. Waterborne pathogens may range in size from about 0.02 micron to more than about 0.1 micron and includes the class of pathogens commonly referred to as "viruses." Many types of waterborne pathogens may be greater than about 0.1 micron in size.

As used herein, the term "amphiphilic protein" refers to proteins having both hydrophobic regions and hydrophilic regions. For example, amphiphilic proteins may be selected from classes of globular and/or random coil proteins. As another example, amphiphilic proteins may be milk proteins. As a further example, amphiphilic proteins may include proteins such as those found in bovine milk including, but not limited to, various caseins and whey proteins.

As used herein, the term "relatively low surface energy" refers to surface energies (i.e., surface free energies) attributed to materials that are not generally considered to be water wettable. Generally speaking, such materials have a surface energy of less than about 45 dynes per centimeter (dynes/cm) as determined in accordance with critical surface tension of wetting techniques described by Bennet, M. K. and Zisman, W. A.; *Relation of Wettability by Aqueous Solutions to the Surface Constitution of Low Energy Solids*; J. Phys. Chem., pps. 1241–1246, Volume 63 (1959). Many such materials have a surface energy of ranging from about 29 to about 35 dynes/cm.

As used herein, the term "relatively high surface tension" refers to a level of attractive force in a liquid exerted by the molecules below the surface upon those at the surface/air interface, resulting from the high molecular concentration of a liquid compared to the low molecular concentration of a gas. Relatively high surface tensions are characteristic of, for example, some aqueous liquids and/or aqueous solutions having little or no added surfactants or other agents that reduce the surface tension. Surface tension may be determined from measurements of the contact angle of sessile drops using a goniometer such as, for example goniometer model No. 100-00 115 (equipped with videocamera) available from Rame-Hart, Inc., or by methods such as, for example, DuNouy ring methods. Relatively high surface tension for the purposes of the present invention is a surface tension of at least about 45 dynes/cm. Desirably, the surface tension is greater than 45 dynes/cm.

As used herein, the term "shear stress conditions" refers to conditions under which a shearing stress (force per unit area) is applied to a liquid. As an example, for a given volume of a liquid, increasing the rate at which the liquid penetrates or passes through a relatively permeable sheet such as, for example, a polyolefin nonwoven fibrous web (i.e., by decreasing the exposure time) results in an increased shear stress at the fiber/liquid interface. In this case, a long exposure time generally indicates little or no shear stresses and a short exposure time generally indicates shear stress conditions. Shear stress conditions may occur in liquid flow having generally laminar or turbulent flow characteristics.

As used herein, the term "adsorbed" refers to a type of adhesion which takes place at the surface of a solid in contact with another medium (e.g., a liquid), resulting in the accumulation or increased concentration of particles, waterborne pathogens and/or molecules from that medium in the immediate vicinity of the surface.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding, wet-forming and various bonded carded web processes.

As used herein, the term "spunbonded web" refers to a web of small diameter fibers and/or filaments which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly dispersed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved Device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the term "microfibers" means small diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

As used herein, the term "apertured film-like material" refers to a generally flat or planar layer of material which has been punched, drilled, apertured, stretched, perforated, embossed, patterned, crinkled and/or otherwise processed so that it has relatively gross or visible openings with or without a pattern or texture in the thickness dimension (i.e., Z-direction) of the material. Exemplary apertured film-like materials include, but are not limited to, perf-embossed films, textured apertured films, reticulated apertured films, contoured apertured films, film-nonwoven apertured laminates, and expanded plexi-filamentary films.

As used herein, the term "sheet" refers to a material that can be a woven fabric, knit fabric, nonwoven fabric or film-like material (e.g., an apertured film-like material).

As used herein, the term "solution" refers to any relatively uniformly dispersed mixture of one or more substances (e.g., solute) in one or more other substances (e.g., solvent). Generally speaking, the solvent may be a liquid such as, for example, water and/or mixtures of liquids. The solvent may contain additives such as salts, acids, bases, viscosity modifiers, preservatives, disinfectants, anti-microbial agents and the like. The solute may be any material adapted to uniformly disperse in the solvent at the appropriate level, (e.g., ionic level, molecular level, colloidal particle level or as a suspended solid). For example, a solution may be a uniformly dispersed mixture of ions, of molecules, of colloidal particles, or may even include mechanical suspensions.

As used herein, the term, "permeable" and "permeability" refer to the ability of a fluid, such as, for example, a gas to pass through a particular porous material. Permeability may be expressed in units of volume per unit time per unit area, for example, (cubic feet per minute) per square foot of material (e.g., ($ft^3$/minute/$ft^2$)). Permeability may be determined utilizing a Frazier Air Permeability Tester available from the Frazier Precision Instrument Company and measured in accordance with Federal Test Method 5450, Standard No. 191A, except that the sample size was 8"×8" instead of 7"×7". Although permeability is generally expressed as the ability of air or other gas to pass through a permeable sheet, sufficient levels of gas permeability may correspond to levels of liquid permeability to enable the practice of the present invention. For example, a sufficient level of gas permeability may allow an adequate level of liquid to pass through a permeable sheet with or without assistance of a driving force such as, for example, an applied vacuum or applied gas pressure. Generally speaking, a permeable sheet may have a permeability of at least about 20 cubic feet per minute per square foot (cfm/$ft^2$), as measured for a substantially dry sheet prior to processing. It is contemplated that a sheet having a permeability of less than about 20 cfm/$ft^2$, as measured for a substantially dry sheet prior to processing, could be used successfully in the practice of the present invention with (or in some cases without) assistance of a driving force such as, for example, an applied vacuum or applied gas pressure. As an example, a permeable sheet may have a permeability of from about 25 to over 200 cfm/$ft^2$, as measured for a substantially dry sheet prior to processing. As another example, a permeable sheet may have a permeability of from about 35 to about 150 cfm/$ft^2$, as measured for a substantially dry sheet prior to processing.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance processability of a composition.

SUMMARY OF THE INVENTION

The problems described above are addressed by the present invention which is directed to a chemically charged-modified filter for removing charged., micron to sub-micron sized particles from an aqueous liquid. The chemically charge-modified filter of the present invention is composed of: 1) a filter sheet having a plurality of individual exposed surfaces, at least a portion of which having a surface energy of less than about 45 dynes per centimeter; 2) amphiphilic macromolecules adsorbed onto at least some individual exposed surfaces having a surface energy of less than about 45 dynes per centimeter; and 3) chemical charge modifiers incorporated onto at least a portion of the amphiphilic macromolecules; so that when said charge-modified substrate is in contact with the aqueous liquid containing the charged, micron to sub-micron sized particles, said particles are adsorbed onto the chemically charge-modified filter.

Generally speaking, the amphiphilic macromolecules adsorbed on the filter sheet have both hydrophobic regions and hydrophilic regions. Useful amphiphilic macromolecules include, but are not limited to, amphiphilic proteins. The amphiphilic proteins may be selected from classes of globular proteins and/or random coil proteins. For example, the amphiphilic proteins may be milk proteins. Desirably, the amphiphilic proteins may include proteins such as those found in bovine milk including, for example, various caseins and whey proteins.

The chemical charge modifiers that are incorporated onto the amphiphilic macromolecule coating may be chemical charge modifiers including, but not limited to, polyvalent cations, cationic polymers, and positively-charged particles. As an example, the chemical charge modifiers may be polyvalent cations including, but not limited to, $Ca^{2+}$, $Al^{3+}$, and $Bi^{3+}$. The chemical charge modifiers may also be positively-charged particles such as, for example, single metal hydroxides, mixed metal hydroxides, and sol-gels. Exemplary positively-charged particles include AlO(OH), Bi(C)H)$_3$ and co-depositions of Fe(OH)$_3$ and Mg(OH)$_2$.

The chemical charge modifiers may also be cationic polymers such as, for example, quaternary amine containing cationic resins, aliphatic amines having at least one primary amine and/or secondary amine, and the like. In one aspect of the invention, the chemical charge modifiers may be cationic polymer systems composed of a primary polymer material and a secondary polymer material. For example, the cationic polymer system may be composed of a primary polymer material such as polyamine epichlorohydrin and a secondary polymer material such as tetraethylene pentamine.

The filter sheet may be a matrix of fibrous material. Suitable matrices of fibrous material may be, for example, woven fabrics, knit fabrics and nonwoven fabrics. The matrix of fibrous material may be a nonwoven fabric such as, for example, nonwoven webs of meltblown fibers, nonwoven webs of continuous spunbond filaments and bonded carded webs. In an embodiment of the invention, the nonwoven web of meltblown fibers may further include one or more secondary materials selected from the group consisting of textile fibers, wood pulp fibers, particulates and superabsorbent materials. The fibrous material may be formed from a thermoplastic polymer. For example, thermoplastic polymer may be selected from polyolefins, polyamides and polyesters. The polyolefin may be selected from polyethylene, polypropylene, polybutene, ethylene copolymers, propylene copolymers, and butene copolymers and blends of the same.

In one aspect of the invention, at least a portion of the fibrous material may be a multi-component or bi-component material selected from multi-component or bi-component fibers and multi-component or bi-component filaments. It is contemplated that at least a portion, if not all, of these fibers may be textured by use of an expanding agent.

The filter sheet may also be a permeable sheet such as an apertured, film-like material. The apertured, film-like material may include, but is not limited to perf-embossed films, one or more textured apertured films, reticulated apertured films, contoured apertured films, film-nonwoven apertured laminates, expanded plexi-filamentary films and combination of the same. The apertured film-like material may further include one or more secondary materials.

The apertured film-like material may be formed from a thermoplastic polymer. For example, the thermoplastic polymer may be selected from polyolefins, polyamides and polyesters. If the polymer is a polyolefin, it may be selected from polyethylene, polypropylene, polybutene, ethylene copolymers, propylene copolymers, and butene copolymers and blends of the same. The permeable sheet may be composed of combinations of one or more matrices of fibrous material and apertured, film-like material.

According to the present invention, the chemically charge-modified filter may have a basis weight of from about 6 to about 400 grams per square meter (gsm). For example, the chemically charge-modified filter may have a basis weight of from about 12 to about 250 grams per square meter. As a further example, the chemically charge-modified sheet may have a basis weight of from about 17 to about 102 grams per square meter.

The present invention encompasses a multi-layer filter material including at least two layers of the chemically charge-modified filter described above. The present invention also encompasses a multi-layer material including at least one layer of the chemically charge-modified filter described above and at least one other layer. The other layer may be selected from woven fabrics, knit fabrics, bonded carded webs, continuous spunbond filament webs, meltblown fiber webs, films, apertured films, and combinations thereof.

The present invention also encompasses a filter in which the chemically charge-modified filter described above is configured into a shape such as, for example, a tube, cylinder, cone, cube, sphere or the like.

The present invention encompasses a method of removing charged, micron to sub-micron sized particles from an aqueous liquid. The method includes the step of passing an aqueous liquid containing charged, micron to sub-micron sized particles through the chemically charge-modified filter described above so that when the aqueous liquid containing charged, micron to sub-micron sized particles is passed through the chemically charge-modified filter, the charged, micron to sub-micron sized particles are adsorbed onto the chemically charge-modified filter.

The present invention encompasses a method of removing a substantial portion of waterborne pathogens from an aqueous liquid contaminated with such waterborne pathogens. The method includes the step of passing the contaminated aqueous liquid through a chemically charge-modified filter composed of: 1) a filter sheet having a plurality of individual exposed surfaces, at least a portion of which having a surface energy of less than about 45 dynes per centimeter; amphiphilic macromolecules adsorbed onto at least some individual exposed surfaces having a surface energy of less than about 45 dynes per centimeter; and chemical charge modifiers incorporated onto at least a portion of the amphiphilic macromolecules, the chemical charge modifiers including: i) a primary charge modifier composed of a water soluble organic polymer having at least one quaternary ammonium group and a molecular weight of greater than about 1000, each monomer of the polymer having at least one epoxide group capable of interacting with to the individual exposed surfaces of the filter sheet modified with amphiphilic macromolecules; and ii) a secondary charge modifier bonded to a portion of the epoxy groups on the organic polymer, wherein the secondary charge modifying agent is an aliphatic polyamine having at least one primary amine and/or secondary amine; so that when the contaminated aqueous liquid is passed through the chemically charge-modified filter, a substantial portion of the waterborne pathogens is adsorbed onto the chemically charge-modified filter. According to an embodiment of the invention, the waterborne pathogens may be greater than 0.1 micron in size. The waterborne pathogens may be, for example, *Vibrio cholerae, Giardia lamblia,* and *Cryptospoidium parvum.*

According to the method of the present invention, the primary charge modifier may be polyamine epichlorohydrin and the secondary charge modifier may be tetraethylene pentamine.

The method of the present invention described above further encompasses a method of removing a substantial portion of waterborne pathogens from water contaminated with such waterborne pathogens to produce potable water. The method includes the step of passing the contaminated water through the chemically charge-modified filter described above so that a substantial portion of the waterborne pathogens is adsorbed onto the chemically charge-modified filter.

DETAILED DESCRIPTION OF THE INVENTION

Figure 1:
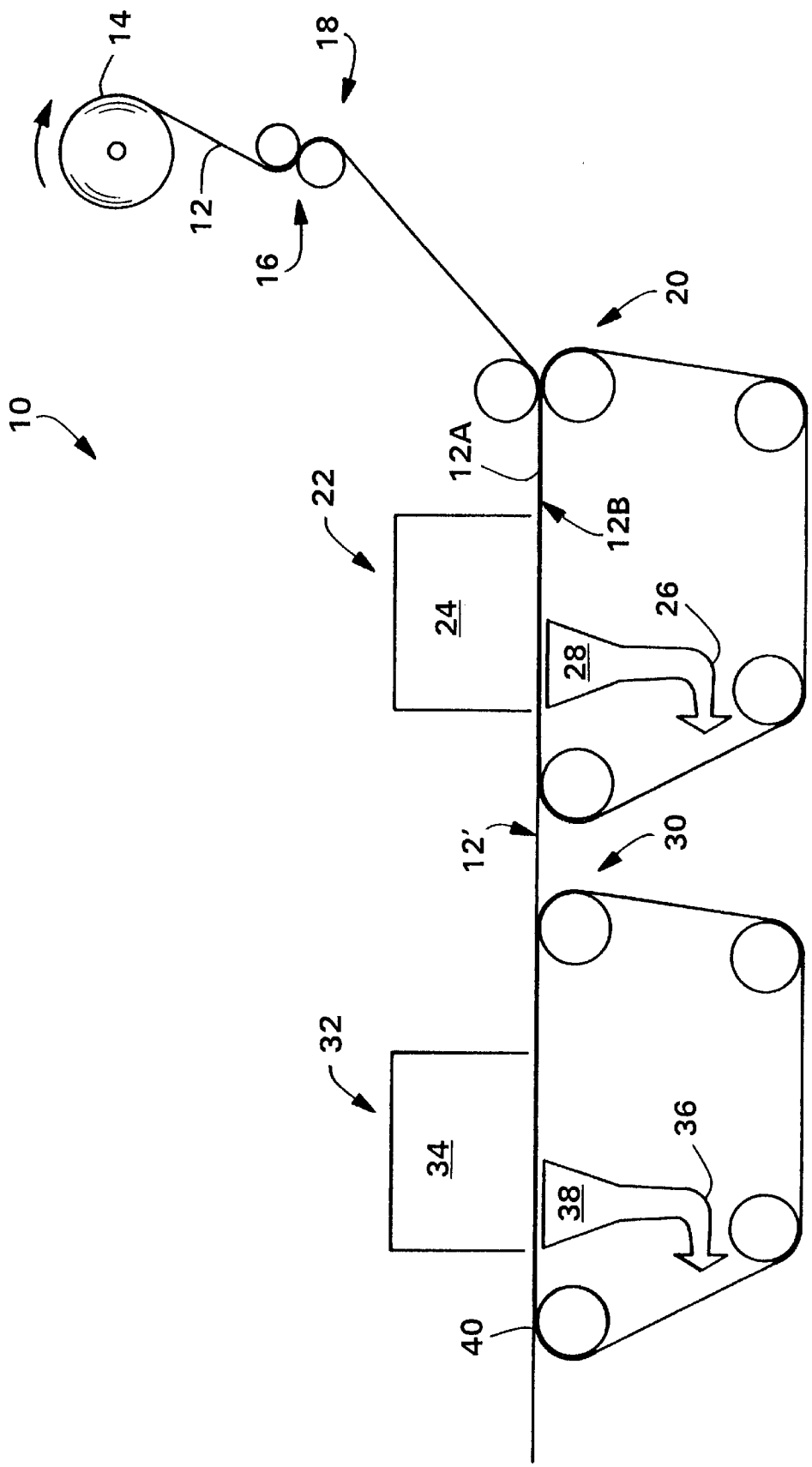
FIG. 1 is an illustration of an exemplary method of applying chemical charge modifiers to a filter sheet to form an exemplary chemically charge-modified filter for removing micron to sub-micron sized particles from an aqueous liquid.

Referring to the drawing and in particular to FIG. 1, there is shown, not necessarily to scale, at 10 an exemplary method of applying chemical charge-modifiers to individual exposed surfaces of a filter sheet (e.g., a matrix of fibrous material or an apertured film-like material) to form an exemplary chemically charge-modified filter for removing micron to sub-micron sized particles from an aqueous liquid. While the invention will be described in connection with desired or preferred embodiments, it will be understood that it is not intended to limit the invention to those embodiments.

According to the present invention, a filter sheet 12 is unwound from a supply roll 14 and travels in the direction indicated by the arrow associated therewith as the supply roll 14 rotates in the direction of the arrows associated therewith. The filter sheet 12 may be formed by one or more sheet making processes and passed directly into the process 10 without first being stored on a supply roll 14. Exemplary sheet-making processes include processes such as meltblowing processes, spunbonding processes, bonded-carded webmaking processes, wet-laying processes, apertured film-forming processes, and the like. The filter sheet may be passed through a pre-treatment station to modify the structure of the sheet. For example, the sheet may be calendered with a flat roll, point bonded or pattern bonded roll and/or aperturing roll in order to achieve desired strength, functional and/or textural properties. Although it is not necessary for the successful deposition of the amphiphilic macromolecule (e.g., amphiphilic protein) coating on the filter sheet in the practice of the present invention, it is contemplated that at least a portion of a surface of the sheet could be modified by various known surface modification techniques prior to entering the continuous process of coating individual exposed surfaces of the filter sheet with amphiphilic proteins. Exemplary surface modification techniques include, for example, chemical etching, chemical oxidation, ion bombardment, plasma treatments, flame treatments, heat treatments, and/or corona discharge treatments.

The filter sheet may be an apertured film-like material. For example, the apertured film-like material may be selected from perf-embossed films, textured apertured films, reticulated apertured films, contoured apertured films, film-nonwoven apertured laminates, and expanded plexifilamentary films.

Alternatively and/or additionally the filter sheet may be a matrix of fibrous material such as one or more woven fabrics, knit fabrics or nonwoven fabrics. That is, the filter sheet may be either an apertured film-like material, a matrix of fibrous material or any suitable combination of the same. If the filter sheet is a nonwoven fabric, it may be a nonwoven fibrous web such as, for example, a bonded carded web, spunbond web, web of meltblown fibers, fibrous batt, fibrous mat and/or multi-ply fibrous web containing the same type of fibrous web or a multiply fibrous web containing different types of fibrous webs. If the filter sheet is a web of meltblown fibers, it may include meltblown microfibers. These nonwoven webs may be formed from thermoplastic polymers or thermoset polymers. If the nonwoven web is formed from a polyolefin, the polyolefin may be polyethylene, polypropylene, polybutene, ethylene copolymers, propylene copolymers and butene copolymers. The fibers and/or filaments may be formed from blends that contain various pigments, additives, strengthening agents, flow modifiers and the like. Such fabrics are described in U.S. Pat. Nos. 4,041,203, 4,374,888, and 4,753,843, the contents of which are incorporated herein by reference. Those patents are assigned to the Kimberly-Clark Corporation, the assignee of the present invention.

The filter sheet may be a nonwoven web that may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, activated carbon, silica, and/or hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. Nos. 4,100,324, and 5,350,624, the disclosure of which is hereby incorporated by reference.

If the filter sheet is a nonwoven web, the fibrous material in the nonwoven web may be joined by interfiber bonding to form a coherent web structure. Interfiber bonding may be produced by entanglement between individual meltblown fibers, carded fibers, spunbond filaments and/or other fibrous materials. Some fiber entangling is inherent in the meltblown process, bonding-carding process and/or spunbond process but may be generated or increased by processes such as, for example, hydraulic entangling or needlepunching. Alternatively and/or additionally a bonding agent may be used to increase the desired bonding. If at least a portion of the fibrous material in the filter sheet is cellulosic fibrous material, some interfiber bonding may be attributable to "paper" bonding.

The filter sheet (either before or after processing) may have a basis weight ranging from about 6 gsm to about 400 gsm. For example, the filter sheet may have a basis weight ranging from about 12 gsm to about 250 gsm. Desirably, the filter sheet may have a basis weight ranging from about 17 gsm to about 102 gsm. It is contemplated that, after processing, any number of treated filter sheets may be joined together or treated filter sheets may be joined to other materials to form a consolidated material that may have a basis weight within the range of 6 gsm to 400 gsm or even greater (e.g., 400 gsm or more).

The filter sheet 12 passes through the nip 16 of an S-roll arrangement 18 in a reverse-S path. From the S-roll arrangement 18, the filter sheet 12 passes to a means for continuously advancing 20 the filter sheet throughout the process. Generally speaking, the means for continuously advancing 20 the filter sheet may be, for example, a moving foraminous belt, a permeable fabric, netting, webbing or the like. It is contemplated that the filter sheet 12 may be self-supporting and need not be transported on a moving belt.

The filter sheet 12 then passes under a means or device for providing an aqueous solution containing amphiphilic macromolecules. Generally speaking, the amphiphilic macromolecules may be amphiphilic proteins. The aqueous solution of amphiphilic macromolecules (e.g., amphiphilic proteins) should have a relatively high surface tension (i.e., the aqueous solution of amphiphilic proteins should have a surface tension of about 45 dyes/cm or greater). The means for providing an aqueous solution containing amphiphilic macromolecules distributes the aqueous solution substantially across and onto a first surface 12A of the continuously advancing filter sheet.

According to the invention, the means or device for depositing the aqueous solution containing amphiphilic macromolecules deposits the amphiphilic macromolecules at conditions under which a shearing stress is applied to the aqueous solution. A description of an exemplary process of applying an amphiphilic macromolecule (e.g., amphiphilic protein) coating to a substrate may be found in U.S. Patent application Ser. No. 08/321,485, entitled "Method of Applying a Protein Coating to a Substrate and Article Thereof", which is assigned to the assignee of the present application, the contents of which are incorporated by reference in their entirety.

The liquid depositing device may be composed of at least one liquid distribution element 24. For example, multiple liquid distribution elements 24 may be arranged in series. The liquid distribution element 24 may be a spillway adapted to produce a stream or shower of the aqueous solution of amphiphilic macromolecules so that it is under shear stress conditions as it contacts the filter sheet. The liquid distribution element 24 may also be one or more nozzles and/or orifices which sprays, squirts, jets or otherwise conveys the aqueous solution so that it is under shear stress conditions as it contacts the filter sheet. It is contemplated that the liquid distribution element may be composed of a reservoir of the aqueous solution of amphiphilic macromolecules designed so that the filter sheet passes over either an interior or exterior surface across one or more openings or orifices which provides contact with the aqueous solution of amphiphilic macromolecules under shear stress conditions. It is also contemplated that the liquid distribution element may be a reservoir of the aqueous solution into which the filter sheet passes at a rate of travel through the reservoir such that shear stress conditions are created at the interface between one or more surfaces of the filter sheet and the aqueous solution.

In one embodiment of the invention, the liquid distribution element may be composed of a reservoir and a spillway adapted to produce a relatively uniform distribution of the aqueous solution to produce a layer of liquid on top of the filter sheet. A vacuum may be applied simultaneously with the deposition of the aqueous solution to generate shear stress conditions in the aqueous solution as it passes through the filter sheet. It is contemplated that application of vacuum may be delayed so that it is not simultaneous with the deposition of aqueous solution. Generally speaking, the vacuum level should be sufficient to draw the aqueous solution through the filter sheet under shear stress conditions. As an example, the vacuum level may be greater than about 60 inches of water. As another example, the vacuum level may range from about 60 to about 270 or more inches of water. A description of an exemplary liquid distribution element may be found in U.S. Pat. No. 5,486,381, which is assigned to the assignee of the present application, the contents of which are incorporated by reference in their entirety.

As discussed above, the means for applying a vacuum 26 to the second surface of the continuously advancing filter sheet are located near the liquid deposition element 24. Generally speaking, the vacuum means 26 may be composed of at least one vacuum element 28. Multiple vacuum elements 28 may be arranged in series. The vacuum element 28 may be a conventional vacuum channel or groove such as, for example, a vacuum slot. The vacuum means 26 should be adapted to handle flow rates/volumes of aqueous solution generally corresponding to the flow rates/volumes out of the liquid deposition means 22.

The liquid deposition means 22 and the vacuum means 26 may be configured to deposit the aqueous solution on the filter sheet 12 in the general form of shapes, patterns, figures, alpha-numeric characters, words, spots, pictures and the like. The vacuum means may contain a variety of configurations such as, for example, unevenly spaced vacuum slots or slits (or shaped openings) designed to produce a gradient deposition. It is contemplated that the liquid deposition means 22 and the vacuum means 26 could be configured to provide intermittent deposition of aqueous solution on the filter sheet so that step-wise or unit-wise operation may be achieved.

Upon application of the vacuum to the second surface 12B of the filter sheet, a substantial portion of the aqueous solution containing amphiphilic macromolecules is drawn from the first surface 12A and substantially through the filter sheet. This passage of the aqueous solution through the filter sheet is generally thought to generate the shear stress conditions necessary to provide appropriate levels of adsorption of amphiphilic macromolecules onto the individual exposed surfaces of the filter sheet.

Generally speaking, evacuation of the aqueous solution of amphiphilic macromolecules under vacuum levels described above to achieve suitable shear stress conditions may be accomplished with a sheet having a permeability of at least about 20 cfm/ft$^2$, as measured for a substantially dry sheet prior to being processed. For example, the permeability of the sheet may range from about 50 to over 200 cfm/ft$^2$, as measured for a substantially dry sheet prior to being processed. If a sheet has inadequate permeability, the aqueous solution may puddle or pool on the first surface and may be non-uniformly concentrated, absorbed or diffused through the sheet. In such cases, it is generally thought that satisfactory conditions could be achieved by applying higher levels of vacuum, higher pressures and/or levels of force to the aqueous solution of amphiphilic macromolecules contacting the filter sheet and/or an applied gas pressure to drive the aqueous solution through the sheet thereby generating the appropriate sheer stress conditions.

According to the present invention, it may be desirable to wash or rinse the filter sheet 12 after being contacted with the aqueous solution of amphiphilic macromolecules. Washing or rinsing (not shown) the coated filter sheet should be carried out using an aqueous liquid having a relatively high surface tension (e.g., water). Although the volume of the liquid wash or rinse may vary greatly, it has been found that a volume of liquid rinse generally similar to the volume of aqueous solution of amphiphilic macromolecules may be satisfactory (e.g., from about 0.5 to about 1.5 times the volume of amphiphilic macromolecule solution).

In general, the aqueous solution of amphiphilic macromolecules should be able to flow freely. For example, the aqueous solution of amphiphilic macromolecules (e.g., amphiphilic proteins) may have a viscosity of from about 0.1 to about 5 centipoise. Lower viscosity solutions appear to be desirable. However, it is contemplated that more viscous aqueous solutions could be used in the practice of the present invention provided that appropriate shear stress conditions can be maintained by techniques including, but not limited to, applying higher levels of vacuum, higher pressures and/or levels of force to the aqueous solution and/or an applied gas pressure.

According to one embodiment of the invention, a substantial portion of the aqueous solution of amphiphilic macromolecules may be drawn through the sheet in less than about 1 or 2 seconds to generate the appropriate shear stress conditions for adsorption. For example, a substantial portion of the aqueous solution may be drawn through the filter sheet in less than about 0.1 second. As a further example, a substantial portion of the aqueous solution may be drawn through the filter sheet in less than about 0.01 second. As yet another example, a substantial portion of the aqueous solution may be drawn through the filter sheet in less than about 0.001 second. It is thought that appropriate shear stress conditions for adsorption of amphiphilic macromolecules may be encountered when the flow of aqueous solution has a Reynold's number of at least about 200. For example, the flow of aqueous solution may have a Reynold's number of at least about 400.

Desirably, the amphiphilic macromolecules are amphiphilic proteins. Generally speaking, the amphiphilic proteins may be selected from classes of globular proteins and/or random coil proteins. For example, the amphiphilic proteins may be milk proteins. Desirably, the amphiphilic proteins may include proteins such as those found in bovine milk including, for example, various caseins and whey proteins.

According to the present invention, milk proteins (e.g., bovine milk proteins) have been identified as well-suited to provide a durable and chemically reactive surface modification when applied to a permeable substrate as describe above. The proteins in milk can be described as generally amphiphilic (i.e., they have both hydrophilic and hydrophobic regions) and tend to be surface active. Beta-casein (β-casein), one of the major milk proteins, is so surface active that it is used as an emulsifier in various food products.

Because these proteins are amphiphilic, they have hydrophobic regions that, in the practice of the present invention, can be readily adsorbed to a polyolefin surface and hydrophilic regions which will orient toward aqueous solution. A wide variety of applications exists for this type of modified surface. For example, the hydrophilic portions of the proteins will impart wettability to relatively hydrophobic substrates (e.g., polyolefin or more particularly, polypropylene substrates) and may serve as a surface primer for attaching other biologically relevant macromolecules such as chitosan and hyaluronic acid.

Although the inventors should not be held to a particular theory of operation, it is thought that certain interfacial free energy phenomena and the application of shear stress to proteins in aqueous solution tend to drive the protein coating (i.e., protein adsorption) on the filter sheet. Generally speaking, random coil proteins (e.g., β-casein) adapt a disordered conformation which minimizes contact of the hydrophobic amino acids of the proteins with water. The overall free energy of the solution is minimized when these hydrophobic areas of the proteins self-associate to screen themselves from the aqueous environment. When exposed to a filter sheet having individual exposed surfaces (some of which having relatively low surface energies) such as, for example, a polyolefin nonwoven, the hydrophobic amino acid groups will have a tendency to associate with the hydrophobic fiber surface, leaving hydrophilic groups oriented toward the aqueous solution and thereby lowering the interfacial energy. These hydrophilic amino acids are thought to be responsible for the improved water wettability of the macromolecule (e.g., protein) modified polyolefin. Although the inventors should not be held to a particular theory of operation, this orientation of the protein at the surface is thought to be the energetically favored state, and explains the tenacious character of the macromolecule (e.g., protein) coatings on the surface (i.e., fiber or film surface).

The application of shear stress to proteins in aqueous solution distorts their thermodynamically favored equilibrium conformation, exposing normally shielded hydrophobic groups to the aqueous solution. This produces an energetically unfavored interface. When in close proximity to a nonwoven fiber surface, these hydrophobic groups are attracted to the hydrophobic polyolefin substrate, which in water is also an energetically unfavored interface, and intermolecular hydrophobic attractions predominate. Adsorption is promoted by a decrease in interfacial free energy. The increase in the number of hydrophobic groups exposed under conditions of increasing shear (i.e. more structural distortion) results in an increased tendency for protein deposition. Without shear distortion, the number of hydrophilic/hydrophobic interactions would be minimized and the chemical nature of the coating would be less desirable for substantive charge modification.

The filter sheet containing a coating of amphiphilic macromolecules (e.g., amphiphilic proteins)—called the coated filter sheet 12' leaves the liquid deposition means 22 and passes to a second means for continuously advancing 30 the coated filter sheet 12'. The second means for continuously advancing 30 the coated filter sheet 12' may be similar to the first means for continuously advancing 20 the filter sheet 12 or may even be unnecessary if the first means for continuously advancing 20 the filter sheet is extended to run through the entire process. It is also contemplated that the filter sheet 12 may be self supporting and need not be transported on a moving belt.

The coated filter sheet 12' passes through a means or device 32 for contacting the sheet 12' with a liquid containing chemical charge modifiers. A description of an exemplary process of applying chemical charge modifiers to an amphiphilic macromolecule (e.g., amphiphilic protein) coated substrate may be found in U.S. patent application Ser. No. 08/548,855, filed on Oct. 25, 1995, entitled "Method of Applying Chemical Charge Modifiers to a Substrate and Article Thereof", the contents of which are incorporated by reference.

The liquid contacting or depositing device 32 may be composed of at least one liquid distribution element 34. For example, multiple liquid distribution elements may be arranged in series. The liquid distribution element 34 may be similar to the liquid distribution element 24. For example, it may be a spillway adapted to produce a stream or shower, or one or more nozzles and/or orifices which sprays, squirts, jets or otherwise conveys the liquid containing the chemical charge modifiers. It is contemplated that the liquid distribution element 34 may be composed of a reservoir of the liquid containing chemical charge modifiers designed so that the coated filter sheet 12' passes over either an interior or exterior surface across one or more openings or orifices which provides contact with the liquid. It is also contemplated that the liquid distribution element may be a reservoir of the aqueous solution into which the coated filter sheet 12' such as, for example, a dip tank or trough. A variety of other reservoir and spillway configurations are contemplated and could generally be determined by one of ordinary skill in the art.

The liquid containing chemical charge modifiers contacts the sheet and the chemical charge modifiers adsorb or become incorporated onto the amphiphilic macromolecule (e.g., amphiphilic protein) coating. For example, when the chemical charge modifiers are polyvalent cations and/or positively charged particles in a liquid having a dielectric constant sufficient for separate charged particles to exist, at least a portion of the cations or positively charged particles become incorporated onto a negatively charged amphiphilic macromolecule (e.g., amphiphilic protein) coating on the coated filter sheet 12 to yield a chemically charge--modified filter sheet 40. Generally speaking, it is desirable that the pH of the liquid containing cationic and/or positively charged chemical charge modifiers should be above the isoelectric point of the amphiphilic macromolecule (e.g., amphiphilic protein) coating on the coated filter sheet 12'. By keeping the pH above the isoelectric point of the amphiphilic macromolecule (e.g., amphiphilic protein) coating, the coating should be negatively charged when the liquid containing oppositely charged chemical charge modifiers contacts the coating. For example, the isoelectric point of milk protein coatings may be present in an aqueous solution of having a pH of about 4. In such case, the liquid containing oppositely charged chemical charge modifiers may have a pH above 4. Of course, it is contemplated that the pH of the aqueous solution may be below the isoelectric point of the amphiphilic macromolecule (e.g., amphiphilic protein) coating so that the coating is positively charged when the liquid containing oppositely charged chemical charge modifiers (i.e., negatively charged chemical charged modifiers) contacts the coating.

The liquid containing the chemical charge modifiers may be a solution, a suspension or the like. For example, the liquid containing the chemical charge modifiers may be a solution of polyvalent cations and/or positively charged particles. As another example, the liquid containing the chemical charge modifiers may be a suspension of positively charged particles. As yet another example, the liquid containing the chemical charge modifiers may be a sol-gel.

The concentration of chemical charge modifiers in solution may vary. As an example, the concentration of chemical charge modifiers in solution may range from about 0.005 to about 5 weight percent. Generally speaking, the viscosity of the liquid containing the chemical charge modifiers should be about that of water.

The chemical charge modifiers may also be cationic polymers such as, for example, quaternary amine containing cationic resins, aliphatic amines having at least one primary amine and/or secondary amine, and the like. In one aspect of the invention, the chemical charge modifiers may be cationic polymer systems composed of a primary polymer material and a secondary polymer material. For example, the cationic polymer system may be composed of a primary polymer material such as polyamine epichlorohydrin and a secondary polymer material such as tetraethylene pentamine. An exemplary primary polymer material is dimethyl amine epichlorohydrin resin (Reten® 201) available from Hercules, Wilmington Del. The primary polymer material may be applied in solution at concentrations that may vary from about 0.04 wt. % up to about 50 wt. %. The secondary polymer material (e.g., tetraethylene pentamine (TEPA)) may also be applied in solution in solution at concentrations that may vary from about 0.01 wt. % to greater than 1 wt. %. For example, the TEPA solution may have a concentration much greater than 1.0 wt. % (e.g., 5 wt. %, 10 wt. % or greater).

Liquid is removed from the chemically charge-modified filter sheet 40 by means for applying a vacuum 36 which may be composed of one or more vacuum elements 38. The design and arrangement of the means for applying a vacuum 36 may be similar to that of the vacuum means 26.

The chemically charge-modified filter sheet 40 may then be passed to a drying operation (not shown). Exemplary drying operations include processes which incorporate infrared radiation, yankee dryers, steam cans, microwaves, hot-air and/or through-air drying techniques, and ultrasonic energy.

The present invention includes a method of removing charged, micron to sub-micron sized particles from aqueous liquid by passing the liquid through the chemically charge-modified filter sheets described above. The charged, micron to sub-micron sized particles may be organic or inorganic or may even be living organisms such as, for example, bacteria. For example, the charge-modified filter sheets may be used to remove charged, micron to sub-micron sized particles from aqueous fluids used in the processing of microelectronic devices, optical components, pharmaceuticals, drugs, medicines, biological materials, and other situations where the absence of such contaminants is desirable. As a further example, the charge-modified filter sheets may be used to remove waterborne pathogens from aqueous liquids contaminated with such waterborne pathogens. The waterborne pathogens may be greater than about 0.1 micron in size. In such applications, the filter sheets of the present invention could be used to generate potable water from water contaminated with waterborne pathogens.

EXAMPLES

Aqueous Amphiphilic Macromolecule Solutions

Aqueous solutions of an amphiphilic macromolecules (i.e., amphiphilic proteins) were prepared for coating a filter sheet with amphiphilic proteins. The solution composition was as follows:

Nonfat Milk:

Carnation® Natural Nonfat Dry Milk (Nestle Food Company) as obtained from local grocery stores was added to hot water (approximately 55°–80° C.) to form various weight percent (0.01, 0.1, 1, 2.5, 8.0) solutions. Water was heated simply to aid in dissolution of the nonfat dry milk. Care was taken to keep the water temperature below 80° C. to avoid reprecipitating the milk solution. Milk solutions were stirred until all solids were dissolved and then stored in a refrigerator until use. Solutions were warmed to room temperature prior to exposure to nonwoven materials. 2.5 percent, by weight, nonfat milk solutions were used as the standard solution for surface modification. Other solutions were used in the study of the concentration dependence of the milk protein deposition.

Solution Contact With A Permeable Substrate (Protein Deposition)

Vacuum Extraction:

The standard procedure used for preparation of protein-coated permeable substrates is described below, and unless otherwise noted, all procedures used (i) the aqueous amphiphilic protein solutions described above; and (ii) a nonwoven web of meltblown polypropylene fibers (referred to as "PP MB") having a basis weight ranging from about 0.5 to about 1.5 ounces per square yard (osy) (about 17 to about 51 gsm) available from Kimberly-Clark Corporation. A disk of the polypropylene meltblown web having a diameter of about 49 mm was placed in a Buchner funnel over a vacuum flask. Approximately 100 mL (milliliters) of the 2.5 percent, by weight, nonfat milk solution at room temperature was introduced into the funnel and passed through the disk of polypropylene meltblown web with the aid of an applied vacuum. In general, the nonfat milk solution wet the polypropylene web for a total exposure time of less than 1 second. The polypropylene web was rinsed with 100 mL of distilled water in the same vacuum extractor apparatus and dried at ambient conditions. Dry add-ons (i.e., the weight of the protein coating) for these small samples were negligible and therefore not recorded.

Solutions Used for Charge Modification:

Milk-protein-treated PP MB was further treated with cationic species such as $Ca^{2+}$, $Al^{3+}$, $Bi^{3+}$, $AlO(OH)$ (boehmite, in sol-gel form), and $Bi(OH)_3$, to produce positively-charged surfaces for particle filtration application. Adsorption of the positive species was confirmed using X-ray photoelectron spectroscopy (referred to as "XPS"). Milk-protein-treated PP MB was prepared as described above. The other solutions used for charge modification are described below:

Aluminum cation:

A 500 ppm $Al^3$, solution, made by diluting (with deionized water) a 10,000 μg/mL aluminum (in HCl) ICP/DCP standard solution (Aldrich Chemical Company), was adjusted to pH 4.2 with sodium hydroxide (NaOH). This solution was used in a study to determine the most efficient method for charge modifying a milk-protein-treated PP MB substrate.

Aluminum cation/nonfat milk:

A 200 ppm $Al^{3+}$, 2.5 wt. % nonfat milk solution was prepared by adding 0.1049 g anhydrous aluminum sulfate $(Al_2(SO_4)_3)$ to 100 g of the nonfat milk solution and stirring for 10 minutes. This was nearly the maximum amount of aluminum sulfate that could be added directly to the nonfat milk solution without causing flocculation. The final pH of the solution was approximately 6.0. This aluminum/milk solution was also used in the study to determine the most efficient method of charge modifying milk-protein-modified PP MB substrates.

Aluminum cation:

A 1000 ppm $Al^{3+}$, 200 mM sodium acetate solution with a pH of 5.0 was prepared by dissolving 13.6 g sodium acetate $(NaCH_3CO_2)$ in 450 mL deionized water and adding 50 mL of a 10,000 μg/mL aluminum ICP/DCP standard solution. Sodium acetate was used to prevent the flocculation caused by raising the pH with hydroxide. Maintaining a pH of 5 increases the incorporation of the aluminum into the milk-protein coating by maintaining sufficient ionization of the carboxylate groups of the protein; pH values of at least 4 were therefore used for the other modifications as well.

Bismuth cation:

1000 ppm bismuth solutions (as $Bi^{3+}$) were prepared by dissolving 27.2 g sodium acetate in 900 mL deionized water and adding 50 mL of 10,000 μg/mL bismuth ICP/DCP standard solution. The resulting precipitate was re-dissolved by adjusting the pH from 4.8 to 4.0 using acetic acid. The solution remained clear after the addition of another 50 mL of the bismuth ICP/DCP standard solution, and its pH was raised from 3.7 to 4.2 with sodium acetate, used to prevent the flocculation caused by raising the pH with hydroxide.

Bismuth Hydroxide:

A 1000 ppm bismuth, 200 mM sodium acetate solution was prepared by dissolving 27.8 g sodium acetate in 900 mL deionized water, adding 100 mL of the bismuth ICP/DCP standard solution, and adjusting the pH to 4.1 with acetic acid. This preparation method yielded a precipitate which was readily suspended in solution for filter media preparation.

Iron/Magnesium Hydroxide:

A mixed metal solution (Fe/Mg) was also prepared and used as a modification in order to promote increased virus adsorption (iron hydroxides have been used to promote virus adsorption in other filter designs) or increased surface area (the mixed metal hydroxides may yield surface areas of 100 $m^2/g$ upon heating to merely 100° C.) . 58.54 g of magnesium sulfate ($MgSO_4 \cdot 7H_2O$) and 3.48 g of iron sulfate ($FeSO_4 \cdot 7H_2O$) were dissolved in 250 mL of Milli-Q deionized water. The solution was heated and stirred for approximately two hours and reached a final temperature of 72° C. before it was diluted (1/10) with deionized water and exposed to the milk-protein-treated PP MB. NaOH (0.8N, 80.5 g NaOH dissolved in 500 mL Milli-Q deionized water and diluted 1/5 before use) was also used during the filter media preparation, as described below.

Cationic Polymers Used for Charge Modification:

Milk-protein-treated PP MB was further treated with cationic polymer to produce positively-charged surfaces for particle filtration application. After the milk-protein treatment, a solution containing dimethyl amine epichlorohydrin resin was applied to the filter using the vacuum extraction procedure described above followed by a solution containing tetraethylene pentamine ("TEPA")using the same vacuum extraction procedure. The treated material was air-dried before testing.

The dimethyl amine epichlorohydrin resin was Reten® 201 available from Hercules, Wilmington Delaware. Approximately 8.0 g Reten® 201 was used to prepare a 0.2 wt. % solution. The pH of the solution was adjusted to 9 using sodium hydroxide. Concentration of the Reten® 201 solution (dimethyl amine epichlorohydrin) may vary from about 0.04 wt. % up to about 50 wt. %. Concentration of the tetraethylene pentamine (TEPA) solution may vary from about 0.01 wt. % to greater than 1 wt. %. For example, the TEPA solution may have a concentration much greater than 1.0 wt. % (e.g., 5 wt. %, 10 wt. % or greater).

Charge Modification of Milk-Protein-Treated PP MB

The standard method of preparing the charge-modified, milk-protein-treated samples involved passing an aliquot of the cationic species solution through a protein-treated PP MB and drying under ambient conditions. Several different cationic species were incorporated into milk-protein coatings to demonstrate the flexibility of the charge-modification process. Incorporation of the positive species was confirmed using XPS and field emission secondary electron microscopy (FESEM). FESEM is well-suited for determining the morphology of the coating on individual nonwoven fibers. Unlike conventional SEM, FESEM does not require a conductive, vapor deposited gold coating to eliminate sample charging. FESEM uses low analysis voltages, and the sample can be examined "as is", with no preparation other than simple mounting. The specifics of each preparation are noted below:

Different Charge Modification Methods

Soak:

A milk-protein-treated PP MB sample was dried and then soaked for one hour in a 500 ppm $Al^{3+}$, solution with a pH of 4.2. The sample was then soaked in approximately 20 mL of water for 5–10 minutes and dried under ambient conditions.

One-Step Vacuum Extraction:

An aliquot (100 mL) of an approximately 200 ppm $Al^{3+}$, 2.5 wt. % nonfat milk solution was passed through one layer of 0.5 osy PP MB in a 49-mm-diameter Buchner funnel apparatus, followed by vacuum extraction of 100 mL of deionized water. The sample was dried under ambient conditions.

Two-Step Vacuum Extraction:

A milk-protein-treated sample was prepared via standard methods and immediately exposed to three passes of a 50-mL aliquot of a 500 ppm $Al^{3+}$ solution at pH 4.2. The sample was rinsed with a 100-mL aliquot of deionized water via vacuum extraction and was dried under ambient conditions. The aluminum solution tested negative for protein (Coomassie blue protein determination) after passage through the milk-protein-treated PP MB sample.

Aluminum-Modified, Milk-Protein-Treated PP MB

Aluminum cation:

Four layers of 0.5 osy PP MB were modified with milk proteins via the standard preparation procedure and were immediately exposed to three passes of a 50-mL aliquot of a 1000 ppm $Al^{3+}$, 200 mM sodium acetate solution at pH 5.0. Coomassie blue dye testing of the aluminum solution after its exposure to the milk-protein-treated sample indicated a removal of trace amounts of protein which were not quantified. The samples were rinsed via vacuum extraction of 100-mL aliquots of deionized water and were dried under ambient conditions.

Aluminum Hydroxide:

In an effort to improve the durability of the aluminum charge modification, deposition of the aluminum functionality as the hydroxide form was undertaken. The two methods used to impart an aluminum hydroxide functionality on milk-protein-treated PP MB are as described below:

In Situ:

A sample previously charge-modified with aluminum as described above was exposed to 30 mL of sodium hydroxide at pH 11 under vacuum extraction conditions and was subsequently rinsed with 50 mL deionized water. The sample was dried under ambient conditions.

Aluminum Sol-gel:

Milk-protein-treated samples were exposed to 2.3 wt. % boehmite aluminum sol-gel either by soaking the sample in the sol-gel solution at a pH of 3.8 or by twice passing a 50 mL aliquot of the sol-gel solution at a pH of 3.8 to 4.3 under vacuum extraction conditions followed by a 200 mL deionized water rinse. The pH of the aluminum sol-gel solution can be raised from 3.8 to 4.2 without precipitation by the addition of sodium acetate. Coomassie blue protein determination indicated that no protein is present in the aluminum sol-gel solution after it is passed through the milk-protein-treated sample.

Bismuth-Modified, Milk-Protein-Treated PP MB

Bismuth Cation:

Two layers of 0.5 osy PP MB were modified with milk proteins via the standard procedure and were immediately exposed to two passes of a 100-mL aliquot of 1000 ppm $Bi^{3+}$ solution at a pH of 4.2, followed by a 100-mL deionized water rinse and drying under ambient conditions. 1000 ppm $Bi^{3+}$ was necessary to ensure sufficient incorporation of bismuth to promote particle adsorption. Using a 500 ppm bismuth solution or a previously-used 1000 ppm bismuth solution did not result in sufficient charge modification to produce significant XPS-detectable bismuth or particle adsorption.

Bismuth Hydroxide:

Two layers of 0.5 osy PP MB were modified with milk proteins via the standard procedure and were immediately exposed to two passes of a 100-mL aliquot of 1000 ppm $Bi^{3+}$ (in the hydroxide form) at pH 4.1, followed by a 100-mL deionized water rinse. The samples were dried under ambient conditions.

Iron/Magnesium Hydroxide-Modified, Milk-Protein -Treated PP MB:

Two layers of 0.5 osy PP MB (49-mm-diameter disks) were treated with milk protein via the standard procedure. An aliquot (100 mL) of the diluted Fe/Mg sulfate solution was then passed through the milk-protein-treated fabrics via vacuum extraction, followed by 100 mL of a 0.8N NaOH solution. The filter was then rinsed with approximately 10 mL deionized water and allowed to dry under ambient conditions. The PP MB assumed a yellow-orange color upon exposure to the Fe/Mg sulfate solution, and this color remained the same after exposure to the NaOH. The color was concentrated in a polka-dot pattern which corresponds to the holes of the Buchner funnel used during the sample preparation.

SAMPLE CHARACTERIZATION

Charge Modification Incorporation and Homogeneity

X-ray Photoelectron Spectroscopy:

X-ray photoelectron spectroscopy (XPS) data were collected using a Surface Science Labs M-Probe ESCA with monochromatic aluminum K-alpha radiation. All samples were mounted on double-side adhesive tape and charge neutralized with a 0.5 eV electron flood. Binding energies were referenced to C(1s) for hydrocarbon at 284.6 eV. XPS-detectable nitrogen was monitored to assess milk-protein modification, while surface aluminum, bismuth, iron, and magnesium were monitored to assess charge modification.

Scanning Electron Microscopy:

Field emission scanning electron microscopy analyses were carried out using a Hitachi S4500 field emission scanning electron microscope.

Wettability and Surface Energy

Contact Angle Measurements:

Contact angles of sessile drops of whole and nonfat milk solutions on a polypropylene film were determined using a Rame-Hart, Inc. goniometer (model number 100-00 115) equipped with a videocamera.

Fluid Surface Tension Reduction:

Meltblown polypropylene webs having a basis weight of 1.5 osy (51 gsm) available from Kimberly-Clark Corporation were milk-protein treated. Samples measuring approximately 2"×3" were soaked for 24 hours in 80 mL of deionized water. The surface tension of the water was measured before and after sample soaking via the DuNouy ring method to determine if wetting of the material occurred via fluid surface tension reduction or by some other mechanism.

Critical Surface Tension of Wetting Measurements:

Approximations of the critical surface tension of wetting of the milk-protein-treated materials were made by testing water wettability and by using wetting tension fluids available from Pillar Technologies, Inc. of Hartland, Wis. Sessile drops of the wetting fluids were placed on milk-protein-modified meltblown polypropylene webs in order of decreasing surface tension. The surface tension of the first drop to spread on the surface of the treated web within 2 seconds yielded an approximation of the treated web's critical surface tension of wetting in dynes/cm (which may be correlated to an approximation of surface energy). See, Bennet, M. K. and Zisman, W. A.; *Relation of Wettability by Aqueous Solutions to the Surface Constitution of Low Energy Solids*; J. Phys. Chem., pps. 1241–1246, Volume 63 (1959).

PARTICLE ADSORPTION TO CHARGE-MODIFIED PP MB

Particle Solutions

Adsorption of inorganic and organic nanoparticles (both positively- and negatively-charged) by the milk-protein-modified and the charge-modified, milk-protein-modified PP MB was conducted to demonstrate the charge-modified PP MB's ability to adsorb a variety of nanoparticle types. Furthermore, nanoparticle adsorption from a variety of solutions was also attempted (bovine blood and 0.9 wt. % NaCl). The zeta-potentials and diameters of the nanoparticles were measured using microelectrophoretic and quasielastic light scattering analyses to confirm the particles' charges and size prior to the adsorption experiments. Microelectrophoretic analysis was conducted on a DELSA 440 analyzer and quasielastic light scattering analysis was conducted on a N4MD analyzer, both available from Coulter Corporation of Hialeah, Fla.

A calibration curve for 300 nM blue polystyrene particles was generated utilizing blue 0.295 $\mu$m diameter polystyrene (PS) particles (Seradyn (Indianapolis, Ind.), #PS/DYBL, Lot #3080). The polystyrene particles at 10 percent solids were diluted to various concentrations with water in volumetric flasks. Dilutions were: 1:400, 500, 1000, 3125, 5000, 10000, 25000, 33000, 50000, 250000, 500000, and 1000000. Measurements were made with a Coulter N4MD submicron particle size analyzer. The following parameters were used with all runs: 90° angle, 300 second run time, 2 runs/sample, and autoranging for sample time and prescale. Counts/second were taken directly from the photodetector of the Coulter N4MD analyzer.

A calculation was performed to determine the number of particles per milliliter of the original sample based on the concentration of PS particles at 10 percent solids and the premise that the particles are substantially spherical.

One mL of the 10 percent solids solution provides 0.1 mL solids. One-tenth (0.1) mL of solids equals approximately 0.1 $cm^3$ solids volume. The radius of individual particles was based on the reported particle diameter of 0.295 $\mu$m which was confirmed via quasielastic light scattering. In particular, the radius of individual particles was 0.295

μm/2×1 cm/10$^4$ μm=1.475×10$^{-5}$ cm. The approximate volume of each particle was then calculated by substituting the radius in the formula for a volume of a sphere (V=⅓ πr$^3$) to yield a volume of 1.344×10$^{-14}$ cm$^3$/particle.

The number of particles per milliliter was then obtained by dividing the total solids volume by the volume per particle. In this situation, the volume 0.1 cm$^3$ was divided by 1.344×10$^{-14}$ cm$^3$/sphere to yield a value of 7.44×10$^{12}$ particles per milliliter.

Figure 2:
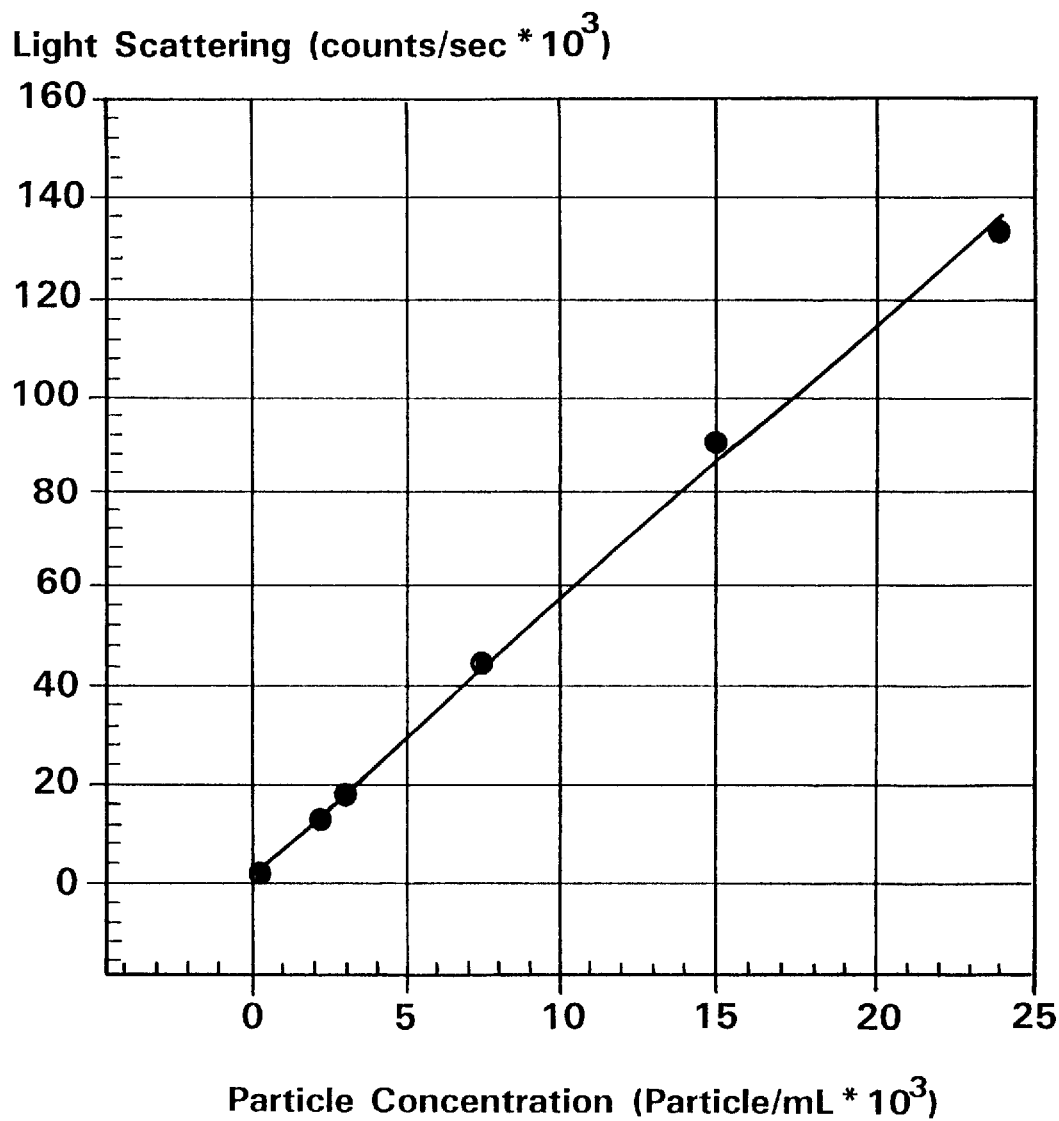
FIG. 2 is a plot of a calibration curve for a particle size analyzer.

The calibration curve used data points from dilutions at 1:250,000, 1:50,000, 1:33,000, 1:25,000, 1:10,000, 1:5,000, and 1:3,125. Concentrations higher and lower than the above dilutions were outside the recommended counts/second range of 5×10$^4$ and 1×10$^6$ for the Coulter N4MD analyzer A plot of the calibration curve is shown in FIG. 2.

Particle adsorption was monitored by XPS, FESEM, and light scattering analyses, and the specific particle solutions used are described below:

Amino-modified polystyrene particles (AMPS, positively-charged, 378 nM) were obtained from Bangs Laboratories, Carmel, IN and were suspended in deionized water to yield a particle concentration of approximately 1×10$^9$ particles/mL.

Aluminum sol-gel particles (positively-charged, 100 nM) were used as suspended in the 2.3 wt. % sol-gel solution.

Polystyrene particles negatively-charged, 300 nM) were obtained from Seradyn, Inc., Indianapolis, Ind. and were suspended in deionized water to yield a final particle concentration ranging from 1×10$^9$ to 7×10$^9$ particles/mL.

Gold colloid (negatively-charged as AuCl$_4^-$, 10 nM) was obtained from Sigma and diluted by a factor of 2 in deionized water to yield a final concentration of approximately 0.005% as HAUCl$_4$.

Particle Adsorption Experiment

The ability of modified filters to adsorb nanoparticles was determined by passing a solution of the particles in water through the one layer of the charge-modified media supported by an untreated layer of 0.5 osy PP MB in a hand-held syringe disk filter apparatus (MILLIPORE 25 mm diameter—available from Millipore Corporation, Bedford, Mass.). A 5 mL aliquot of particle solution was passed through the media in approximately 30 seconds, followed by air to remove any excess liquid. The filter media was then rinsed with a 5–20 mL volume of deionized water to remove any loosely-bound particles, which was then followed again by air to remove any excess liquid. The light scattering intensity (λ=632.8 nM) of the particle solution at an angle of 90° was measured with a Coulter N4MD analyzer before and after its passage through the filter, and the number of particles/mL calculated from calibration curves determined previously. Gold colloid and aluminum sol-gel particle adsorption was monitored using XPS. Samples were submitted for SEM analysis to determine the uniformity and amount of particle adsorption to individual fibers.

The adsorption of particles from saline and bovine blood (hematocrit 30%) was also qualitatively assessed by adding approximately 500 μL of standard particle solution (300 nM diameter) to 10 mL of 0.9 wt. % saline or 10 mL of bovine blood, passing 5 mL of the solution through an aluminum sol-gel charge-modified filter as described above, and rinsing with 10 mL deionized water.

EXPERIMENTAL RESULTS

Particle Adsorption

Demonstration of Particle Adsorption

The utility of the charge modifications to the PP MB described above in adsorbing a wide variety of particle types is summarized in Tables 1 and 2. Average amounts of particle adsorption ranged from 12% to 30%, with absolute values for the number of particles adsorbed given in the tables.

Milk-protein-modified PP MB, with a negative surface charge, has adsorbed positively-charged inorganic and organic particles from water (an untreated PP MB control did not adsorb such particles). As indicated in Table 1, the milk-protein-modified fibers adsorb approximately 3.2×10$^{10}$ amino-modified polystyrene particles from solution per gram of filter.

Charge modification of the milk-protein-treated PP MB yields a positive surface capable of adsorbing negatively-charged organic and inorganic particles from solution. As outlined in Table 1, aluminum sol-gel modified and bismuth hydroxide modified materials exhibit adsorption of 3.5×10$^{13}$ (86 nM) and 1.2×10$^{11}$ (300 nM) polystyrene particles per gram of filter, respectively, from solution, while milk-protein-treated PP MB alone exhibits no significant particle adsorption. The observed differences in the absolute number of particles adsorbed likely relates to the initial particle concentration and not necessarily the charge modification or the particle size. Table 2 indicates the successful adsorption of negatively-charged gold colloid particles via XPS detection of gold on the filter surface. X-ray photoelectron spectroscopy (XPS) was used to monitor particle adsorption because the 10-nM diameter particle adsorption could not be detected by the light scattering and FESEM analyses conducted.

In addition to adsorbing particles from water, aluminum sol-gel modified PP MB is capable of adsorbing negatively-charged polystyrene particles from 0.9 wt. % saline and bovine blood. The presence of a blue color on filters exposed to the 300-nM, blue-dye-containing polystyrene particles in solution indicates particle adsorption.

Composite Filter for Particle Adsorption

A filter combining layers of negatively-charged and positively-charged, milk-protein-modified PP MB should be capable of adsorbing both positively- and negatively-charged particles from solution. Preliminary experiments were conducted in which a particle solution of both negatively- and positively-charged particles was exposed to a composite filter consisting of a positively-charged, bismuth-modified layer and a negatively-charged, milk-protein-modified layer (particles passed first through the positively-charged layer and then the negatively-charged layer). These experiments indicate that filtration of both negatively-- and positively-charged particles using a composite filter media may be possible; however, negatively-charged particles were observed on both layers of filter media. FESEM analyses of the milk-protein-modified (only) layer do indicate the presence of both the 378-nM amino-modified polystyrene particles and the 300-nM polystyrene particles. Optimization of this type of filter design is necessary.

Uniformity of Particle Adsorption

Figure 3A:
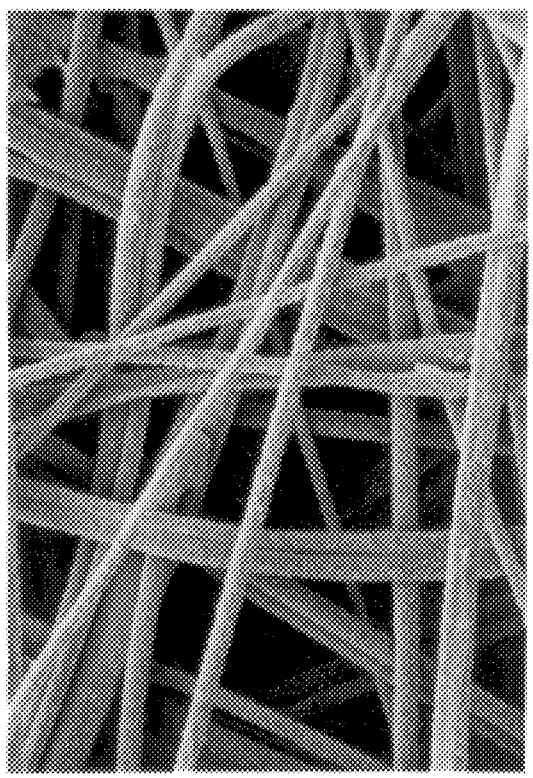
FIG. 3A is a micrograph of an exemplary chemically charge-modified filter.
Figure 3B:
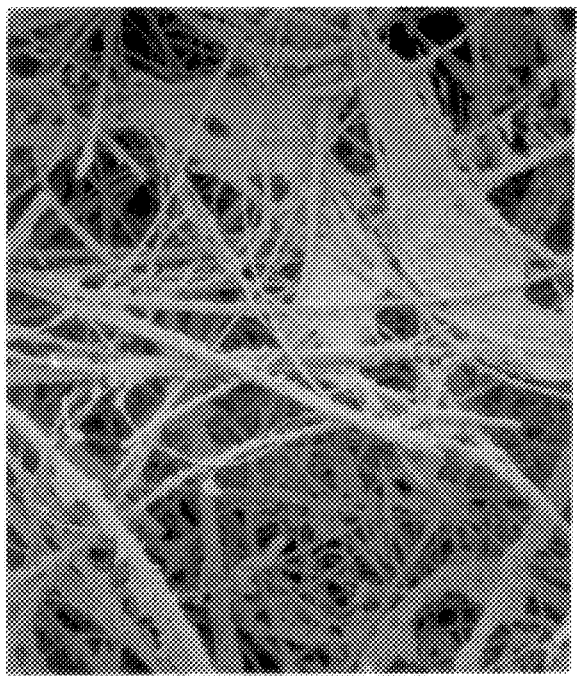
FIG. 3B is a micrograph of a charge-modified/glass cellulose filter.

FIGS. 3A and 3B illustrate the comparable uniformity of particle adsorption for an aluminum-modified (Al$^{3+}$), milk-protein-treated PP MB (FIG. 3A) versus a commercially-available, charge-modified glass/cellulose filter medium (Virosorb® 1MDS, CUNO, Inc., Meriden, Conn.) (FIG. 3B). FIG. 3A is a 1000× linear magnification photomicrograph and FIG. 3B is a 1050× linear magnification photomicrograph. Five mL of approximately $1.7 \times 10^9$ particles/mL solution was passed through the filter media followed by a deionized water rinse. Polystyrene particles, 300-nM in diameter, were used in these experiments. From these micrographs it is evident that although the uniformity of the particle adsorption is similar, the commercially-available filter exhibits significantly greater particle adsorption. The increased surface area of the commercially-available filter likely promotes a greater amount of particle adsorption/mass of filter media. It is also probable that an increased charge density for the commercially-available filter contributes to the increase particle adsorption as well.

Figure 4A:
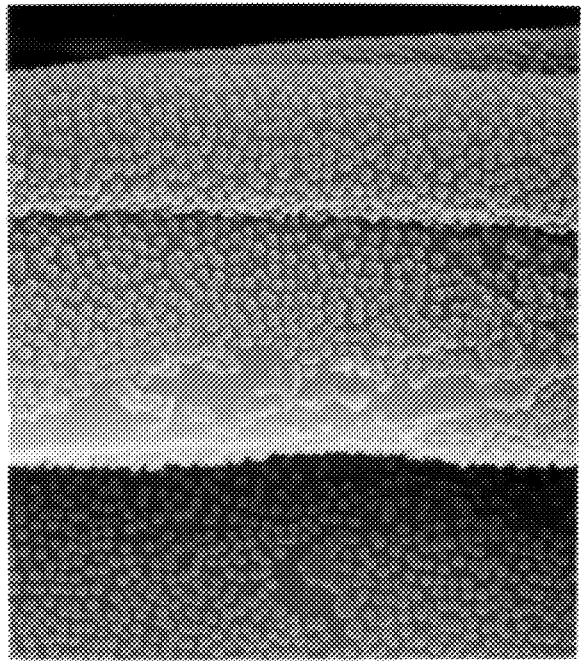
FIGS. 4A and 4B are micrographs of exemplary chemically charge-modified filters.
Figure 4B:
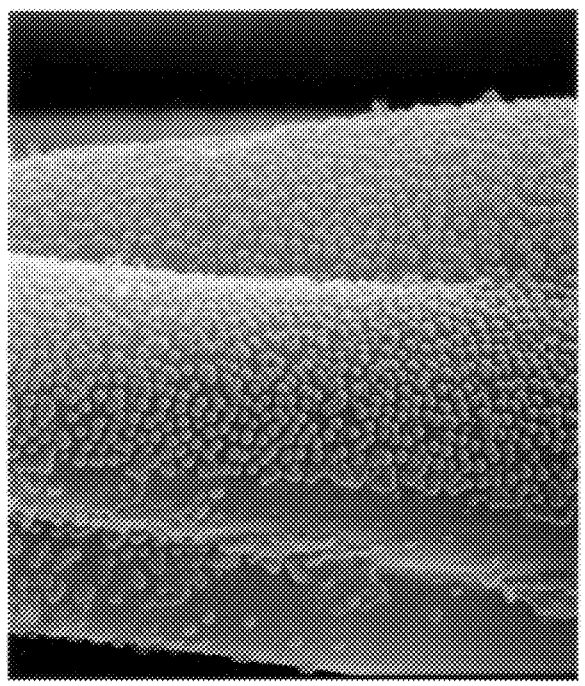

Particle adsorption is not only uniform over the surface of the filters, but also through the depth of the filter medium, as illustrated in FIGS. 4A and 4B for 86-nM diameter particle adsorption to aluminum sol-gel modified media ($3.5 \times 10^{13}$ particles per gram of filter). The filters were exposed to 5 mL of particle solution with a concentration of approximately $1 \times 10^{12}$ particles/mL and rinsed with deionized water. The filter was immersed in liquid nitrogen and cut with a razor blade. The cross-section was scanned, and representative photographs of the top and bottom of the filter were taken. Note the even distribution of particles along the fibers and the similarity in the amount of coverage between the two photographs, indicating particle adsorption throughout the depth of the charge-modified PP MB. FIG. 4A is a 12,000× linear magnification photomicrograph from the top of the filter cross-section and FIG. 4B is a 12,000 linear magnification photomicrograph from the bottom of the filter cross-section.

Figure 5A:
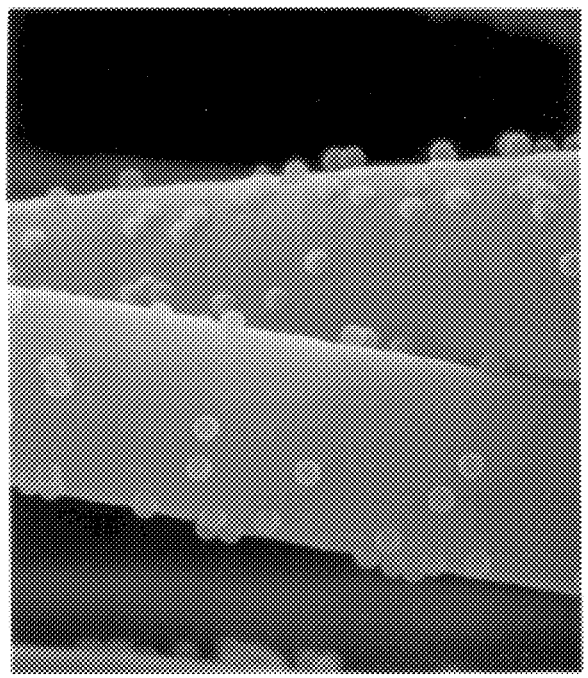
FIGS. 5A and 5B are micrographs of exemplary chemically charge-modified filters.
Figure 5B:
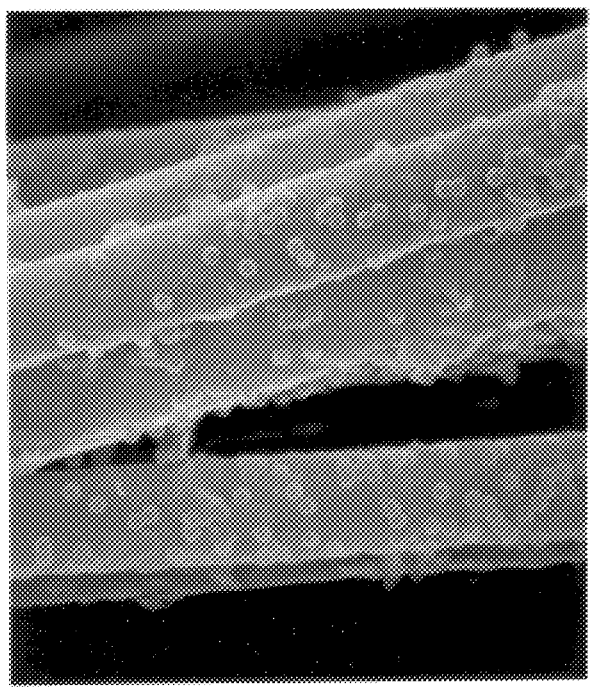

While the photographs shown are for an aluminum sol-gel modified media, similar results are expected for the bismuth-modified media, based on the similarities in particle adsorption illustrated in FIGS. 5A and 5B (300-nM particles on the charge modified filters; $1.5 \times 10^{11}$ particles per gram of filter). FIG. 5A is a 12,000× linear magnification photomicrograph of an aluminum sol-gel modified, milk-protein treated PP MB and FIG. 5B is an 8,000× linear magnification photomicrograph of a bismuth hydroxide modified, milk-protein treated PP MB. Samples were prepared and particle adsorption undertaken as described in the experimental section. The density of this particle coverage is similar between the two photographs indicating the similarities in the charge-modifications' particle adsorption capabilities. The density of particle coverage for these samples is less than that shown for the 86-nM-diameter particles in FIGS. 4A and 4B because the initial particle concentration was lower. The density of particle coverage shown here is similar to that shown at lower magnification for the $Al^{3+}$, charge modification in FIG. 3A.

Figure 6A:
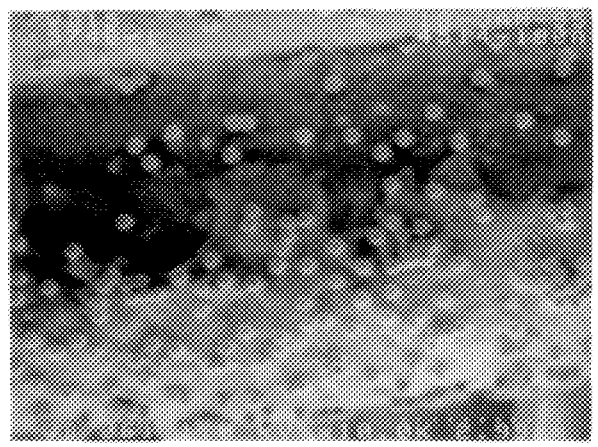
FIGS. 6A, 6B and 6C are micrographs of exemplary chemically charge-modified filters.
Figure 6B:
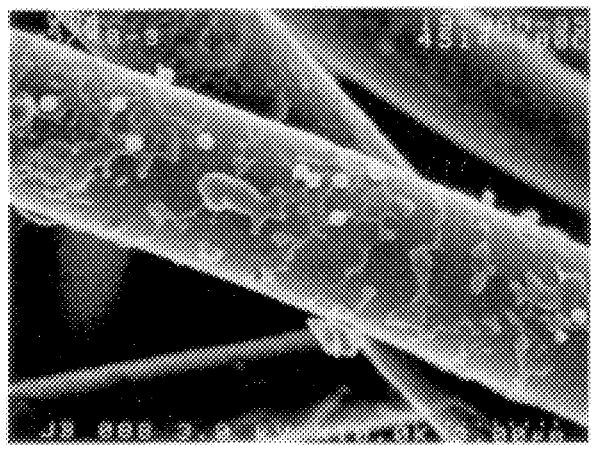
Figure 6C:
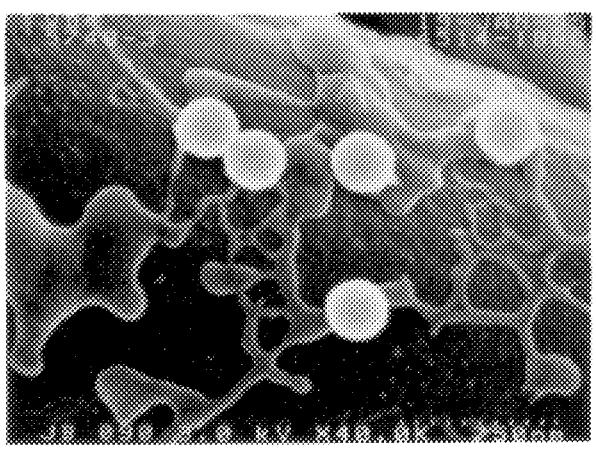

FIGS. 6A, 6B and 6C demonstrate that the particles, while adsorbed relatively uniformly over the fiber surface, are specifically adsorbed on the fibers in regions which exhibit the greatest amount of coating coverage. Samples were prepared and particle adsorption undertaken as described in the experimental section. Note that the particle coverage correlates with the presence of the charge modification; particles are adsorbed only in areas which exhibit the charge modified coating and not randomly over the fiber surface. FIG. 6A is a 10,000× linear magnification photomicrograph of bismuth hydroxide modified, milk-protein-treated PP MB with 300-nM diameter polystyrene particles from a $2.7 \times 10^{10}$ particles/mL solution. FIG. 6B is 10,000× linear magnification photomicrograph is of bismuth hydroxide modified, milk-protein-treated PP MB with 300-nM diameter polystyrene particles from $2.7 \times 10^9$ particles/mL solution. Note the decrease in the amount of particle adsorption with the decrease in particle concentration, as compared to FIG. 6A. This can be seen in FIG. 6C which is a 40,000× linear magnification photomicrograph of the material shown in FIG. 6B. This evidence corroborates that there are interactions between the charge-modifier coating and the particles which are responsible for particle adsorption and not just random interactions of the particles with the unmodified fiber surface. Overall, FESEM studies indicate that all of the charge modifications promote uniform particle adsorption over the charge-modified fiber surface, with the particles specifically associated with the charge-modifier coating on the fibers and not just randomly adsorbed.

Concentration Dependence Of Particle Adsorption

The discrepancy in the amount of particle coverage observed for the samples in FIGS. 4 (A & B) and FIGS. 5 (A & B) most likely results from the difference in initial concentrations of the two particle solutions. As may also be seen by comparing FIG. 6A and 6B, a greater initial particle concentration results in a greater amount of particle adsorption. This effect likely results from the increased number of interactions with the fiber surface caused by the increased number of particles per unit volume. It does not appear to be caused by the difference in the absolute number of particles exposed to the filter surface, as laboratory observations indicate that increasing the volume of a dilute particle solution does not increase particle adsorption significantly.

Waterborne Pathogen Adsorption

Chemically charge-modified filters of the present invention exhibit an ability to remove substantial portions of waterborne pathogens from aqueous liquid contaminated with such waterborne pathogens. For purposes of the present invention, the expression "removing a substantial portion of waterborne pathogens from water contaminated with such waterborne pathogens" generally refers to removal of at least about 90 percent of the waterborne pathogens. In many instances, the removal rate will be significantly greater. For example, in some cases removal rates of 99 percent (a log 2 reduction) have been achieved. Removal rates of 99.9 percent (log 3 reduction), 99.99 percent (log 4 reduction), 99.999 percent (log 5 reduction) or even greater have been achieved.

The filters of the present invention remove waterborne pathogens primarily by chemical and electrokinetic interactions between the surface charge on the filter material and the pathogens rather than by physical entrapment. Evidence that this is the case may be found in a comparison of the effective equivalent pore size of various filter material.

Measurements were made of the effective equivalent diameter of pores in three different types of filter material. Pore sizes were determined by liquid displacement techniques utilizing a Coulter Porometer and Coulter PORO-FIL™ test liquid available from Coulter Electronics Limited, Luton, England. The mean flow pore size is determined by wetting a test sample with a liquid having a very low surface tension (i.e., Coulter POROFIL™). Air pressure is applied to one side of the sample. Eventually, as the air pressure is increased, the capillary attraction of the fluid in the largest pores is overcome, forcing the liquid out and allowing air to pass through the sample. With further increases in the air pressure, progressively smaller and smaller holes will clear. A flow versus pressure relationship for the wet sample can be established and compared to the results for the dry sample. The mean flow pore size is measured at the point where the curve representing 50% of the dry sample flow versus pressure intersects the curve representing wet sample flow versus pressure. The diameter of the pore which opens at that particular pressure (i.e., the mean flow pore size) can be determined from the following expression:

Pore Diameter (Microns)=(40τ)/pressure where τ=surface tension of the fluid expressed in units of mN/M; the pressure is the applied pressure expressed in millibars (mbar); and the very low surface tension of the liquid used to wet the sample allows one to assume that the contact angle of the liquid on the sample is about zero. Of course, for structures such as those existing in conventional nonwoven fabrics, the measured pore diameters are not absolute values of pore size. Nevertheless, the measured pore diameters are useful for relative comparisons of pore size distributions between dissimilar materials.

The mean flow pore diameter was measured for a polypropylene meltblown nonwoven having a basis weight of about 1.5 osy (~51 gsm); a Millipore 0.5 micron filter available from Millipore Corporation, Bedford, Mass.; and a 1.5 osy milk-protein-treated polypropylene meltblown nonwoven further treated with Reten® 201 and TEPA charge modifiers. The results of pore size testing are reported in Table 3. The MILLIPORE filter has a mean flow pore size of about 35 times smaller than the 1.5 osy (~51 gsm) polypropylene meltblown nonwoven used in the present invention. The charge modified polypropylene meltblown showed essentially the same pore size characteristics as the untreated meltblown web indicating that the milk-protein treatments and the cationic resin charge modifiers did not block or reduce the pore size characteristics of the material.

*Vibrio cholerae* and *E. coli* Filtration

Reten® 201/TEPA (dimethyl amine epichlorohydrin/tetraethylene pentamine) modified, milk-protein-treated polypropylene meltblown filters having a basis weight of about 1.5 osy (~51 gsm) were tested for their ability to filter or remove *Vibrio cholerae* from aqueous solution. The *Vibrio cholerae* were plated and an isolated colony was inoculated in 5 mL of sterile tryptic soy buffer which was incubated at 35 degrees Centigrade for 3 hours. The *Vibrio cholerae* solution was measured at 420 nM and diluted until the absorbance was 0.64 for an approximate titer of $1\times10^8$ waterborne pathogens per mL. One mL of the *Vibrio cholerae* solution was added to one liter of sterile water for an approximate initial titer of $1\times10^5$ per mL.

Reten® 201/TEPA modified, milk-protein-treated polypropylene filters having a diameter of 48 mm were placed in a filter vacuum apparatus. Approximately forty (40) mL of the cholera solution was filtered through the filters. The filtrate was serially diluted by adding 1 mL of filtrate to 9 mL of phosphate buffer solution (NaCl, $Na_2HPO_4$, $KH_2PO_4$ and $dH_2O$) . Approximately 0.1 mL of each dilution (0, −1, −2, −3, −4) was plated on 1% tryptic soy agar plates. The plates were incubated for 15 hours.

Control *Vibrio cholerae* solutions which were not filtered grew 65 cfu and 71 cfu at a 1:100 dilution. From this data, it was determined that the initial titer was approximately $3.40\times10^6$ organisms per milliliter.

No colonies were found on the plates containing the filtrate solutions. Accordingly, the filters provided greater than a 6.5 log reduction in the concentration of *Vibrio Cholerae*. As can be seen from this example, the Reten® 201/TEPA modified, milk-protein-treated meltblown polypropylene nonwoven filters were found to work particularly well at removing *Vibrio cholerae* from water. Results of the experiments are reported in Table 4.

The experiment was repeated for the Reten® 201/TEPA modified, milk-protein-treated meltblown polypropylene nonwoven filters using the same procedure except that the *Vibrio cholerae* solutions contained NaCl at varying concentrations. The *Vibrio cholerae* solutions contained NaCl at concentrations of 100 parts per million (ppm), 500 parts per million (ppm) and 1000 parts per million (ppm). Results of the experiments are reported in Table 5. As can be seen from Table 5, the Reten® 201/TEPA modified, milk-protein-treated meltblown polypropylene nonwoven filters removed *Vibrio cholerae* from water containing up to 1000 ppm NaCl.

The procedure described above was used to measure the ability of the Reten® 201/TEPA milk-protein-treated meltblown polypropylene nonwoven filters to remove *E. coli* from solution. The results are reported in Table 5. As can be seen from Table 5, the Reten® 201/TEPA modified, milk-protein-treated meltblown polypropylene nonwoven filters were found to work particularly well at removing *E. coli* from water.

*Giardia lamblia* and *Cryptosporidium parvum* Filtration

A flat circular disc having a diameter of 25 mm was cut from a sheet of 1.5 osy (~51 gsm) Reten® 201/TEPA, modified, milk-protein-treated meltblown polypropylene filter material. Similar discs were cut from a control (untreated) meltblown polypropylene filter material. Individual discs were placed in a conventional syringe filter holder for testing.

Suspensions of *Giardia lamblia* cysts and *Cryptosporidium parvum* oocysts were prepared. The *Giardia lamblia* and *Cryptosporidium parvum* were obtained from DYNA genics (13026 N. Cave Creek Road, Suite 101, Phoenix, Ariz. 85022). Suspension densities were determined with a hemocytometer and phase contrast microscopy (PCM). Concentrations of the suspensions were adjusted to $1\times10^6$ cysts or oocysts per mL.

Approximately 50 mL of deionized water was spiked with 0.1 mL of the suspension to obtain a total concentration of $2\times10^3$ cysts or oocysts per mL.

The suspension was passed through the filter using the syringe and filter holder apparatus at a flow rate of 5 mL per minute.

The filtrate was centrifuged (1000× g for 15 minutes for *Cryptosporidium parvum* and 5 minutes for *Giardia lamblia*)to sediment the cyst or oocysts. The filtrate was reduced to 1.0 mL by removing the supernatant via aspiration.

Cysts or oocysts were enumerated by visualization in a hemocytometer. If the count of the cysts or oocysts in the filtrate were low, the entire filtrate was stained using Immunofluorescent Assay (IFA).

Percent removal was calculated by the following formula:

% Removal=(Suspension Conc.)−(Filtrate Conc.)×100 (Suspension Conc.)

The results of the filtration efficiency tests are reported in Tables 6 and 7. As can be seen from these Tables, the charge-modified, milk-protein-treated meltblown polypropylene nonwoven filters appear to work particularly well in removing *Giardia lamblia*, and *Cryptosporidium parvum* from water.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

TABLE 1

Particle Adsorption
To Charge Modified, Milk Protein Treated PP MB[1]

| Sample | Particle, | Size, | Charge | Scattering Intensity Initial c/s | Scattering Intensity Final c/s | # Particles[2] Adsorbed/gram filter |
|---|---|---|---|---|---|---|
| Untreated PP MB | AMPS[3], | 378 nm, | positive | $2.18 \times 10^5$ | $2.14 \times 10^5$ | Negligible |
| Milk protein treated PP MB | AMPS, | 378 nm, | positive | $2.3 \times 10^5$ | $2.0 \times 10^5$ | $3.2 \times 10^{10}$ |
| Milk protein treated PP MB | PS[4], | 300 nm, | negative | $3.6 \times 10^5$ | $3.5 \times 10^5$ | Negligible |
| $Al^{3+}$ modified PP MB | PS, | 300 nm, | negative | $9.9 \times 10^4$ | $4.3 \times 10^4$ | $2.6 \times 10^{11}$ |
| AlO(OH) modified PP MB | PS, | 300 nm, | negative | $3.6 \times 10^5$ | $3.1 \times 10^5$ | Not calc'd[6] |
| AlO(OH) modified PP MB | PS, | 86 nm, | negative | $4.5 \times 10^5$ | $4.0 \times 10^5$ | $3.5 \times 10^{13}$ |
| $Bi(OH)_3$ modified PP MB | PS, | 300 nm, | negative | $2.3 \times 10^5$ | $2.0 \times 10^5$ | $1.2 \times 10^{11}$ |
| Fe/Mg hydroxide modified PP MB | PS, | 300 nm, | negative | $1.3 \times 10^5$ | $1.2 \times 10^5$ | $5.0 \times 10^{10}$ |

[1]Particle adsorption experiments were carried out as described in the experimental section. Light scattering values are given for scattering at 90°.
[2]The number of particles was calculated from nephelometric calibration curves for the polystyrene particles.
[3]Amino modified polystyrene particles, obtained from Bangs Laboratories, Carmel, IN.
[4]Polystyrene particles, obtained from Seradyn, Inc., Indianapolis, IN. The particles are negatively-charged due to residual sulfate groups present from the persulfate initiator used in the emulsion polymerization.
[5]Although there was a slight decrease in the light scattering intensity for this sample, there was no blue color visible on the filter. The slight decrease in light scattering intensity for the Fe/Mg hydroxide sample, however, was accompanied by a very distinct blue color on the filter.
[6]These values were not calculated because the light scattering intensity values were outside of the range of the calibration curve. The increased particle concentration was purposely selected to maximize particle adsorption for SEM analyses.

TABLE 2

Evidence for Adsorption of Gold Colloid[1]
to Charge Modified Nonwovens

| Sample | % Element | Au(4f) | N(1s) | C(1s) | O(1s) |
|---|---|---|---|---|---|
| Milk protein treated control | N/A | ND[2] | 11.3 | 73.1 | 15.7 |
| AlO(OH) modification | 12.1 (Al) | 0.4[3] | 5.5 | 54.1 | 27.9 |
| $Bi(OH)_3$ modification | 3.8 (Bi) | 0.1[3] | 6.3 | 74.1 | 15.8 |

[1]In contrast to other particle adsorption experiments, XPS was used to monitor adsorption of gold colloid particles as $AuCl_4$, because their adsorption could not be detected via light scattering or FESEM analyses.
[2]Not Detected. All values reported are the average of two measurements.
[3]A pink color arising from the gold colloid (as $AuCl_4^-$) solution was visually evident on these samples as well, but not on the milk-protein-treated control.

TABLE 3

Results of Coulter Porometer Tests

| Sample | Minimum Size (μm) | Maximum Size (μm) | Mean Flow Pore size (μm) |
|---|---|---|---|
| Millipore 0.5 mm Filter | 0.30 | 0.82 | 0.48 |
| Meltblown Polypropylene 1.5 osy (~51 gsm) | 8.19 | 43.55 | 12.81 |
| Reten ® 201/TEPA modified Meltblown Polypropylene 1.5 osy (~51 gsm) | 8.33 | 42.75 | 13.38 |

TABLE 4

Vibrio Cholerae Filter Test Results

| Filter | Vibrio Cholerae log reduction | Original Titer cfu/mL | % Reduction |
|---|---|---|---|
| Untreated polypropylene meltblown | 0 | $6.0 \times 10^4$ | 0 |
| Reten ® 201/TEPA modified milk-protein treated polypropylene meltblown 1 | >6.5 | $3.4 \times 10^6$ | >99.99994 |

TABLE 5

Vibrio Cholerae and E. Coli Filter Test Results

| Micro-organism | Experimental Conditions | Initial CFU/mL | Final CFU/mL | % Reduction | Log Reduction |
|---|---|---|---|---|---|
| V. Cholerae | 1000 ppm NaCl | $5.0 \times 10^5$ | $1.4 \times 10^2$ | 99.97% | 3.6 |
| V. Cholerae | 500 ppm NaCl | $1.2 \times 10^5$ | $1.5 \times 10^3$ | 98.7% | 1.9 |
| V. Cholerae | 100 ppm NaCl | $2.6 \times 10^4$ | $4.7 \times 10^3$ | 82% | 0.7 |
| E. coli | | $5.7 \times 10^5$ | 0 | 100% | >5.8 |

TABLE 6

Giardia lamblia Cyst Filter Test Results

| Filter | Suspension Count (cysts per filter) | Filtrate Count (hemocytometer) | Filtrate Count (IFA) | % Reduction |
|---|---|---|---|---|
| Control Replicate 1 | $1.6 \times 10^5$ | $4.0 \times 10^3$ | >1000 | 97.5 |
| Control Replicate 2 | $1.6 \times 10^5$ | $4.3 \times 10^3$ | >1000 | 97.3 |
| Test Replicate 1 | $1.6 \times 10^5$ | 0 | 0 | >99.9994 |
| Test Replicate 2 | $1.6 \times 10^5$ | 0 | 0 | >99.9994 |

TABLE 7 uz,5/28 Cryptosporidium parvum OOcyst Filter Test Results

| Filter | Suspension Count (oocysts per filter) | Filtrate Count (hemocytometer) | Filtrate Count (IFA) | % Reduction |
|---|---|---|---|---|
| Control Replicate 1 | $0.7 \times 10^5$ | $0.9 \times 10^4$ | >1000 | 87.1 |
| Control Replicate 2 | $0.7 \times 10^5$ | $1.9 \times 10^4$ | >1000 | 72.9 |
| Test Replicate 1 | $0.7 \times 10^5$ | 0 | 0 | >99.998 |
| Test Replicate 2 | $0.7 \times 10^5$ | 0 | 0 | >99.9998 |

What is claimed is:

1. A chemically charged-modified filter for removing charged, micron to sub-micron sized particles from an aqueous liquid, said chemically charge-modified filter comprising:
  a filter sheet having a plurality of individual exposed surfaces, at least a portion of which having a surface energy of less than about 45 dynes per centimeter;
  amphiphilic macromolecules adsorbed onto at least some individual exposed surfaces having a surface energy of less than about 45 dynes per centimeter; and
  chemical charge modifiers incorporated onto at least a portion of the amphiphilic macromolecules,
  so that when said chemically charge-modified filter is in contact with the aqueous liquid containing the charged, micron to sub-micron sized particles, said particles are adsorbed onto the chemically charge-modified filter.

2. The chemically charge-modified filter of claim 1, wherein the amphiphilic macromolecules are amphiphilic proteins.

3. The chemically charge-modified filter of claim 2, wherein the amphiphilic proteins are selected from the group consisting of globular proteins and random coil proteins.

4. The chemically charge-modified filter of claim 2, wherein the amphiphilic proteins are selected from milk proteins.

5. The chemically charge-modified filter of claim 1, wherein the chemical charge modifiers are selected from polyvalent cations, cationic polymers, and positively-charged particles.

6. The chemically charge-modified filter of claim 5, wherein the polyvalent cations are selected from $Ca^{2+}$, $Al^{3+}$, and $Bi^{3+}$.

7. The chemically charge-modified filter of claim 5, wherein the positively-charged particles are selected from single metal hydroxides, mixed metal hydroxides, and sol-gels.

8. The chemically charged-modified filter of claim 5, wherein the cationic polymers comprise quaternary amine containing cationic resins.

9. The chemically charged-modified filter of claim 8, wherein the cationic polymers further comprise aliphatic polyamines having at least one primary amine and/or secondary amine.

10. The chemically charge-modified filter of claim 9, wherein the cationic polymers comprise a primary polymer material composed of polyamine epichlorohydrin and a secondary polymer material composed of tetraethylene pentamine.

11. The chemically charge-modified filter of claim 1, wherein the filter sheet is a matrix of fibrous material.

12. The chemically charge-modified filter of claim 1, wherein the matrix of fibrous material is selected from woven fabrics, knit fabrics and nonwoven fabrics.

13. The chemically charge-modified filter of claim 1, wherein the filter sheet is an apertured, film-like material.

14. The chemically charge-modified filter of claim 13, wherein the apertured, film-like material is selected from perf-embossed films, textured apertured films, reticulated apertured films, contoured apertured films, film-nonwoven apertured laminates, and expanded plexi-filamentary films.

15. A multilayer filter material comprising at least two layers of the chemically charge-modified filter of claim 1.

16. A multilayer filter material comprising at least one layer of the chemically charged modified filter material of claim 1 and at least one other layer.

17. The chemically charge-modified filter of claim 1, wherein the chemically charge-modified filter is adapted, when in contact with water containing waterborne pathogens, to adsorb the waterborne pathogens onto the chemically charge-modified filter.

18. The chemically charge-modified filter of claim 17, wherein the chemically charge-modified filter is adapted, when in contact with water containing waterborne pathogens greater than about 0.1 microns in size, to adsorb the waterborne pathogens onto the chemically charge-modified filter.

19. A chemically charged-modified filter for removing charged, micron to sub-micron sized particles from an aqueous liquid, said chemically charged-modified filter comprising:
  a filter sheet having a plurality of individual exposed surfaces, at least a portion of which having a surface energy of less than about 45 dynes per centimeter;
  amphiphilic proteins adsorbed onto at least some individual exposed surfaces having a surface energy of less than about 45 dynes per centimeter; and
  chemical charge modifiers incorporated onto at least a portion of the amphiphilic macromolecules;
  so that when said chemically charge-modified filter is in contact with the aqueous liquid containing the charged, micron to sub-micron sized particles, said particles are adsorbed onto the chemically charge-modified filter.

20. A method of removing charged, micron to sub-micron sized particles from an aqueous liquid, said method comprising passing an aqueous liquid containing charged, micron to sub-micron sized particles through a chemically charge-modified filter comprising:

a filter sheet having a plurality of individual exposed surfaces, at least a portion of which having a surface energy of less than about 45 dynes per centimeter;

amphiphilic macromolecules adsorbed onto at least some individual exposed surfaces having a surface energy of less than about 45 dynes per centimeter; and chemical charge modifiers incorporated onto at least a portion of the amphiphilic macromolecules;

so that when the aqueous liquid containing charged, micron to sub-micron sized particles is passed through the chemically charge-modified filter, the charged, micron to sub-micron sized particles are adsorbed onto the chemically charge-modified filter.

21. A method of removing charged, micron to sub-micron sized particles from an aqueous liquid, said method comprising passing an aqueous liquid containing charged, micron to sub-micron sized particles through a chemically charge-modified filter comprising:

a filter sheet having a plurality of individual exposed surfaces, at least a portion of which having a surface energy of less than about 45 dynes per centimeter;

amphiphilic proteins adsorbed onto at least some individual exposed surfaces having a surface energy of less than about 45 dynes per centimeter; and chemical charge modifiers incorporated onto at least a portion of the amphiphilic proteins;

so that when the aqueous liquid containing charged, micron to sub-micron sized particles is passed through the chemically charge-modified filter, the charged, micron to sub-micron sized particles are adsorbed onto the chemically charge-modified filter.

22. A method of removing a substantial portion of waterborne pathogens from an aqueous liquid contaminated with such waterborne pathogens, the method comprises passing the contaminated aqueous liquid through a chemically charge-modified filter comprising:

a filter sheet having a plurality of individual exposed surfaces, at least a portion of which having a surface energy of less than about 45 dynes per centimeter;

amphiphilic macromolecules adsorbed onto at least some individual exposed surfaces having a surface energy of less than about 45 dynes per centimeter; and chemical charge modifiers incorporated onto at least a portion of the amphiphilic macromolecules, said chemical charge modifiers comprising:

a primary charge modifier comprising a water soluble organic polymer having at least one quaternary ammonium group and a molecular weight of greater than about 1000, each monomer of the polymer having at least one epoxide group capable of interacting with the individual exposed surfaces of the filter sheet modified with amphiphilic macromolecules; and a secondary charge modifier bonded to a portion of the epoxy groups on the organic polymer, wherein the secondary charge modifying agent is an aliphatic polyamine having at least one primary amine and/or secondary amine;

so that when the contaminated aqueous liquid is passed through the chemically charge-modified filter, a substantial portion of the waterborne pathogens are adsorbed onto the chemically charge-modified filter.

23. The method of claim 22, wherein the primary charge modifier is polyamine epichlorohydrin and the secondary charge modifier is tetraethylene pentamine.

24. The method of claim 22, wherein the waterborne pathogens are greater than about 0.1 micron in size.

25. The method of claim 22, wherein the waterborne pathogens are selected from *Vibrio cholerae, Giardia lamblia*, and *Cryptosporidium parvum*.

26. The method of claim 25, wherein the reduction of *Vibrio cholerae* is greater than a log 3 reduction.

27. The method of claim 22, wherein the filter sheet is a matrix of fibrous material.

28. The method of claim 27, wherein the matrix of fibrous material is selected from woven fabrics, knit fabrics and nonwoven fabrics.

29. The method of claim 22, wherein the filter sheet is an apertured, film-like material.

30. The method of claim 29, wherein the apertured, film-like material is selected from perf-embossed films, textured apertured films, reticulated apertured films, contoured apertured films, film-nonwoven apertured laminates, and expanded plexi-filamentary films.

31. The method of claim 22, wherein the filter sheet has a cylindrical form.

32. A method of removing a substantial portion of waterborne pathogens from water contaminated with such waterborne pathogens to produce potable water, the method comprises passing the contaminated water through a chemically charge-modified filter comprising:

a filter sheet having a plurality of individual exposed surfaces, at least a portion of which having a surface energy of less than about 45 dynes per centimeter;

amphiphilic proteins adsorbed onto at least some individual exposed surfaces having a surface energy of less than about 45 dynes per centimeter; and chemical charge modifiers incorporated onto at least a portion of the amphiphilic proteins, said chemical charge modifiers comprising:

a primary charge modifier comprising a water soluble organic polymer having at least one quaternary ammonium group and a molecular weight of greater than about 1000, each monomer of the polymer having at least one epoxide group capable of interacting with the individual exposed surfaces of the filter sheet modified with amphiphilic proteins; and a secondary charge modifier bonded to a portion of the epoxy groups on the organic polymer, wherein the secondary charge modifying agent is an aliphatic polyamine having at least one primary amine and/or secondary amine;

so that when the contaminated water is passed through the chemically charge-modified filter, a substantial portion of the waterborne pathogens is adsorbed onto the chemically charge-modified filter to yield potable water.

33. The method of claim 32, wherein the amphiphilic proteins are selected from the group consisting of globular proteins and random coil proteins.

34. The method of claim 33, wherein the amphiphilic proteins are selected from milk proteins.

35. The method of claim 32, wherein the primary charge modifier is polyamine epichlorohydrin and the secondary charge modifier is tetraethylene pentamine.

36. The method of claim 32, wherein the waterborne pathogens are greater than about 0.1 micron in size 37. The method of claim 32, wherein the waterborne pathogens are selected from *Vibrio cholerae, Giardia lamblia*, and *Cryptosporidium parvum*.

* * * * *